United States Patent [19]
Head et al.

[11] Patent Number: 6,093,696
[45] Date of Patent: Jul. 25, 2000

[54] TYROSINE DERIVATIVES

[75] Inventors: John Clifford Head; Sarah Catherine Archibald, both of Maidenhead; Graham John Warrellow, Northwood, all of United Kingdom

[73] Assignee: Celltech Therapeutics, Limited, United Kingdom

[21] Appl. No.: 09/086,421

[22] Filed: May 29, 1998

[30] Foreign Application Priority Data

May 30, 1997 [GB] United Kingdom .................... 9711143
Oct. 27, 1997 [GB] United Kingdom .................... 9722674

[51] Int. Cl.⁷ ........................ A61K 31/425; A61K 38/05; C07D 277/06; C07K 5/078
[52] U.S. Cl. ............................ 514/19; 514/365; 548/200; 548/201
[58] Field of Search ...................... 514/19, 365; 548/200, 548/201

[56] References Cited

U.S. PATENT DOCUMENTS

| | | | |
|---|---|---|---|
| 4,987,132 | 1/1991 | Mase et al. | 514/252 |
| 5,164,372 | 11/1992 | Matsuo et al. | 514/19 |

FOREIGN PATENT DOCUMENTS

| | | |
|---|---|---|
| 0 031 104 A1 | 7/1981 | European Pat. Off. |
| 0 048 763 A1 | 4/1982 | European Pat. Off. |
| 0 322 068 A1 | 6/1989 | European Pat. Off. |
| 0 394 989 A2 | 10/1990 | European Pat. Off. |
| WO 86/02353 | 4/1986 | WIPO |
| WO 94/15954 | 7/1994 | WIPO |
| WO 94/15955 | 7/1994 | WIPO |
| WO 95/13811 | 5/1995 | WIPO |
| WO 95/15973 | 6/1995 | WIPO |
| WO 95/35314 | 12/1995 | WIPO |
| WO 96/01644 | 1/1996 | WIPO |
| WO 96/22966 | 8/1996 | WIPO |
| WO 97/03094 | 1/1997 | WIPO |
| WO 97/04247 | 2/1998 | WIPO |
| WO 98/04913 | 2/1998 | WIPO |
| WO 98/53814 | 12/1998 | WIPO |
| WO 98/53817 | 12/1998 | WIPO |
| WO 98/53818 | 12/1998 | WIPO |
| WO 98/58902 | 12/1998 | WIPO |
| WO 99/06390 | 2/1999 | WIPO |
| WO 99/06431 | 2/1999 | WIPO |
| WO 99/06432 | 2/1999 | WIPO |
| WO 99/06433 | 2/1999 | WIPO |
| WO 99/06434 | 2/1999 | WIPO |
| WO 99/06435 | 2/1999 | WIPO |
| WO 99/06436 | 2/1999 | WIPO |
| WO 99/06437 | 2/1999 | WIPO |
| WO 99/10312 | 3/1999 | WIPO |
| WO 99/10313 | 3/1999 | WIPO |
| WO 99/20272 | 4/1999 | WIPO |

OTHER PUBLICATIONS

Corey, E.J. et al., "A Synthetic Method for Formyl→Ethynyl Conversion (RCHO→RC≡CH or RC≡CR')", *Tetrahedron Lett.*, 1972, 36, 3769–3772.

Lei, H. et al., "Efficient Synthesis of a Phosphinate Bis–Amino Acid and Its Use in the Construction of Amphiphilic Peptides", *J. Org. Chem.*, 1994, 59, 4206–4210.

Nagasawa, H.T. et al., "β–Substituted Cysteines as Sequestering Agents for Ethanol–Derived Acetaldehyde in Vivo", *J. Med. Chem.*, 1987, 30, 1373–1378.

Osborne, L., "Leukocyte Adhesion to Endothelium in Inflammation", *Cell*, 1990, 62, 3–6.

Abraham, W.M. et al., "$\alpha_4$–Integrins Mediate Antigen–Induced Late Bronchial Responses and Prolonged Airway Hyperresponsiveness in Sheep", *J. Clin. Invest.*, 1994, 93, 776–787.

Berlin, E. et al., "$\alpha 4\beta 7$ Integrin Mediates Lymphocyte Binding to the Mucosal Vascular Addressin MAdCAM–1", *Cell*, 1993, 74, 185–195.

(List continued on next page.)

*Primary Examiner*—Jeffrey E. Russel
*Attorney, Agent, or Firm*—Woodcock Washburn Kurtz Mackiewicz & Norris LLP

[57] ABSTRACT

Tyrosine derivatives of formula (1) are described:

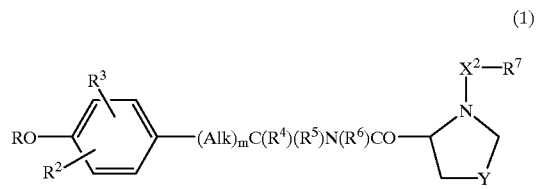

(1)

in which
R is (1) a group $R^1X^1$— where $R^1$ is an optionally substituted alkyl or aromatic group, and $X^1$ is a covalent bond or a —$(CH_2)_n$—[where n is an integer 1 or 2], —C(O)—, —$CH_2C(O)$—, —NHC(O)—, —$CH_2NHC(O)$—, or —$SO_2$— group, or (2) a group $(Hal^1)_3CSO_2$—, where $Hal^1$ is a fluorine or chlorine atom;
$R^2$ and $R^3$, which may be the same or different, is each a hydrogen or halogen atom or an alkyl, alkoxy, hydroxyl or nitro group;
Alk is an alkylene chain;
m is zero or an integer 1;
$R^4$ is a hydrogen atom or a methyl group;
$R^5$ is a group —$(CH_2)_pCO_2R^8$ where p is zero or an integer 1 and $R^8$ is a hydrogen atom or an alkyl group;
$R^6$ is a hydrogen atom or an alkyl group;
Y is a sulphur atom or a —$S(O)_q$— group where q is an integer 1 or 2;
$X^2$ is a —C(O)—, —C(O)O—, —CONH— or —$S(O)_2$— group;
$R^7$ is an optionally substituted alkyl group or an aryl or aralkyl group;
and the salts, solvates and hydrates thereof.

The compounds are able to inhibit the binding of $\alpha_4$ integrins to their ligands and are of use in the prophylaxis and treatment of immune or inflammatory disorders.

20 Claims, No Drawings

OTHER PUBLICATIONS

Binnis, R.M. et al., "The Role of E–Selectin in Lymphocyte and Polymorphonuclear Cell Recuritment into Cutaneous Delayed Hypersensitivity Reactions in Sensitized Pigs", *J. Immunol.*, 1996, 157, 4094–4099.

Briskin, M.J. et al., "Structural Requirements for Mucosal Vascular Addressin Binding to Its Lymphocyte Receptor $\alpha_4\beta_7$", *J. Immunol.*, 1996, 156, 719–726.

Cardarelli, P.M. et al., "Cyclic RGD Peptide Inhibits $\alpha 4\beta 7$ Interaction with Connecting Segment 1 and Vascular Cell Adhesion Molecule", *J. Biol. Chem.*, 1994, 269(28), 18668–18673.

Ferguson, T.A. et al., "Two integrin–binding peptides abrogate T cell–mediated immune responses in vivo", *Proc. Natl. Acad. Sci. USA*, 1991, 88, 8072–8076.

Holzmann, B. et al., "Peyer's patch–specific lymphocyte homing receptors consist of a VLA–4–like $\alpha$ chain associated with either of two integrin $\beta$ chains, one of which is novel", *EMBO J.*, 1989, 8(6), 1735–1741.

Humphries, M.J. et al., "Mechanisms of VCAM–1 and fibronectin binding to integrin $\alpha_4\beta_1$: implications for integrin function and rational drug design", *Ciba Foundations Symposium*, 1995, 189, 177–194.

Issekutz, T.B., "Inhibition of Lymphocyte Endothelial Adhesion and In Vivo Lymphocyte Migration to Cutaneous Inflammation by TA–3, a New Monoclonal Antibody to Rat LFA–1", *J. Immunol.*, 1992, 149(10, 3394–3402.

Li, Z. et al., "Effect of an anti–Mol MAb on ozone–induced airway inflammation and airway hyperresponsiveness in dogs", *Am. J. Physiol.*, 1992, 263(6 Pt 1), L723–726.

Marlin, S.D. et al., "LFA–1 Immunodeficiency Disease", *J. Exp. Med.*, 1986, 164, 855–867.

Osborn, L. et al., "Direct Expression Cloning of Vascular Cell Adhesion Molecule 1, a Cytokine–Induced Endothelial Protein that Binds to Lymphocytes", *Cell*, 1989, 59, 1203–1211.

Podolsky, D.K. et al., "Attenuation of Colitis in the Cotton–top Tamarin by Anti–$\alpha$4 integrin Monoclonal Antibody", *J. Clin. Invest.*, 1993, 92, 372–380.

Shroff, H.N. et al., "Small Peptide Inhibitors of $\alpha_4\beta_7$ Mediated MAdCAM–1 Adhesion to Lymphocytes", *Barge. Med. Chem. Letts.*, 1996, 6(21), 2495–2500.

Sonnenberg, A., "Integrins and Their Ligands", *Curr. Topics Microbiol. Immunol.*, 1993, 184, 7–35.

Springer, T.A., "Adhesion receptors of the immune system", *Nature*, 1990, 346, 425–434.

Springer, T.A., "Traffic Signals for Lymphocyte Recirculations and Leukocyte Emigration: The Multistep Paradigm", *Cell*, 1994, 76, 301–314.

Vanderslice, P. et al., "A Cyclic Hexapeptide is a Potent Antagonist of $\alpha$4 Integrins", *J. Immunol.*, 1997, 158, 1710–1718.

Yang, X., "A predominant role of integrin $\alpha$4 in the spontaneous development of autoimmune diabetes in nonobese diabetic mice", *Proc. Natl. Acad. Sci. USA*, 1994, 91, 12604–12608.

Yednock, T.A., "Prevention of experimental autoimmune encephalomyelitis by antibodies against $\alpha 4\beta 1$ integrin", *Nature*, 1992, 356, 63–66.

WPI/Derwent No. XP–002076854, Japanese Patent No. JP 04 193 895 A (Ajinomoto, K.K.) Jul. 13, 1992, DW9234, 1 Page, Abstract Only.

WPI/Derwent No. XP–002076855, Japanese Patent No. JP 56 049 373 A (Dainippon Pharm Co Ltd), May 2, 1981, DW8125, 1 Page, Abstract Only.

SEQUENCE LISTING

<160> NUMBER OF SEQ ID NOS: 4

<210> SEQ ID NO 1
<211> LENGTH: 3
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 1

Leu Asp Val
  1

<210> SEQ ID NO 2

```
<211> LENGTH: 3
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 2

Ile Asp Ala
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 3

Arg Glu Asp Val
  1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 4

Gln Ile Asp Ser Pro
  1               5
```

TYROSINE DERIVATIVES

This invention relates to a series of tyrosine derivatives, to compositions containing them, to processes for their preparation, and to their use in medicine.

Over the last few years it has become increasingly clear that the physical interaction of inflammatory leukocytes with each other and other cells of the body plays an important role in regulating immune and inflammatory responses [Springer, T A. Nature, 346, 425, (1990); Springer, T. A. Cell 76, 301, (1994)]. Many of these interactions are mediated by specific cell surface molecules collectively referred to as cell adhesion molecules.

The adhesion molecules have been sub-divided into different groups on the basis of their structure. One family of adhesion molecules which is believed to play a particularly important role in regulating immune and inflammatory responses is the integrin family. This family of cell surface glycoproteins has a typical non-covalently linked heterodimer structure. At least 14 different integrin alpha chains and 8 different integrin beta chains have been identified [Sonnenberg, A. Current Topics in Microbiology and Immunology, 184, 7, (1993)]. The members of the family are typically named according to their heterodimer composition although trivial nomenclature is widespread in this field. Thus the integrin termed $\alpha 4\beta 1$ consists of the integrin alpha 4 chain associated with the integrin beta 1 chain, but is also widely referred to as Very Late Antigen 4 or VLA4. Not all of the potential pairings of integrin alpha and beta chains have yet been observed in nature and the integrin family has been subdivided into a number of subgroups based on the pairings that have been recognised [Sonnenberg, A. ibid].

The importance of cell adhesion molecules in human leukocyte function has been further highlighted by a genetic deficiency disease called Leukocyte Adhesion Deficiency (LAD) in which one of the families of leukocyte integrins is not expressed [Marlin, S. D. et al J. Exp. Med. 164, 855 (1986)]. Patients with this disease have a reduced ability to recruit leukocytes to inflammatory sites and suffer recurrent infections which in extreme cases may be fatal.

The potential to modify adhesion molecule function in such a way as to beneficially modulate immune and inflammatory responses has been extensively investigated in animal models using specific monoclonal antibodies that block various functions of these molecules [e.g. Issekutz, T. B. J. Immunol. 3394, (1992); Li, Z. et al Am. J. Physiol. 263, L723, (1992); Binns, R. M. et al J. Immunol. 157, 4094, (1996)]. A number of monoclonal antibodies which block adhesion molecule function are currently being investigated for their therapeutic potential in human disease.

One particular integrin subgroup of interest involves the $\alpha 4$ chain which can pair with two different beta chains $\beta 1$ and $\beta 7$ [Sonnenberg, A. ibid]. The $\alpha 4\beta 1$ pairing occurs on many circulating leukocytes (for example lymphocytes, monocytes and eosinophils) although it is absent or only present at low levels on circulating neutrophils. $\alpha 4\beta 1$ binds to an adhesion molecule (Vascular Cell Adhesion Molecule-1 also known as VCAM-1) frequently up-regulated on endothelial cells at sites of inflammation [Osborne, L. Cell, 62, 3, (1990)]. The molecule has also been shown to bind to at least three sites in the matrix molecule fibronectin [Humphries, M. J. et al. Ciba Foundation Symposium, 189, 177, (1995)]. Based on data obtained with monoclonal antibodies in animal models it is believed that the interaction between $\alpha 4\beta 1$ and ligands on other cells and the extracellular matrix plays an important role in leukocyte migration and activation [Yednock, T. A. et al, Nature, 356, 63, (1992); Podolsky, D. K. et al. J. Clin. Invest. 92, 373, (1993); Abraham, W. M. et al. J. Clin. Invest. 93, 776, (1994)].

The integrin generated by the pairing of $\alpha 4$ and $\beta 7$ has been termed LPAM-1 [Holzmann, B and Weissman, I. EMBO J. 8, 1735, (1989)] and like $\alpha 4\beta 1$, binds to VCAM-1 and fibronectin. In addition, $\alpha 4\beta 7$ binds to an adhesion molecule believed to be involved in the homing of leukocytes to mucosal tissue termed MAdCAM-1 [Berlin, C. et al, Cell, 74, 185, (1993)]. The interaction between $\alpha 4\beta 7$ and MAdCAM-1 may also be important at sites of inflammation outside of mucosal tissue [Yang, X -D. et al, PNAS, 91, 12604 (1994)].

Regions of the peptide sequence recognised by $\alpha 4\beta 1$ and $\alpha 4\beta 7$ when they bind to their ligands have been identified. $\alpha 4\beta 1$ seems to recognise LDV SEQ ID NO:1, IDA SEQ ID NO:2 or REDV SEQ ID NO:3 peptide sequences in fibronectin and a QIDSP SEQ ID NO:4 sequence in VCAM-1 [Humphries, M. J. et al, ibid] whilst $\alpha 4\beta 7$ recognises a LDT sequence in MAdCAM-1 [Briskin, M. J. et al, J. Immunol. 156, 719, (1996)]. There have been several reports of inhibitors of these interactions being designed from modifications of these short peptide sequences [Cardarelli, P. M. et al J. Biol. Chem. 269, 18668, (1994); Shroff, H. N. Bioorganic. Med. Chem. Lett. 6, 2495, (1996); Vanderslice, P. J. Immunol. 158, 1710, (1997)]. It has also been reported that a short peptide sequence derived from the $\alpha 4\beta 1$ binding site in fibronectin can inhibit a contact hypersensitivity reaction in a trinitrochlorobenzene sensitised mouse [Ferguson, T. A. et al, PNAS 88, 8072, (1991)].

Since the alpha 4 subgroup of integrins are predominantly expressed on leukocytes, inhibition of their ligand binding abilities can be expected to be beneficial in a number of immune or inflammatory disease states. However, because of the ubiquitous distribution and wide range of functions performed by other members of the integrin family it is very important to be able to identify inhibitors which will selectively inhibit the binding of the alpha 4 subgroup.

We have now found a group of compounds which are potent and selective inhibitors of the binding of $\alpha 4$ integrins to their ligands. Members of the group are able to inhibit the binding of $\alpha 4$ integrins such as $\alpha 4\beta 1$ and/or $\alpha 4\beta 7$ to their ligands at concentrations at which they generally have no or minimal inhibitory action on x integrins of other subgroups. The compounds are thus of use in medicine, for example in the prophylaxis and treatment of immune or inflammatory disorders as described hereinafter.

Thus according to one aspect of the invention we provide a compound of formula (1)

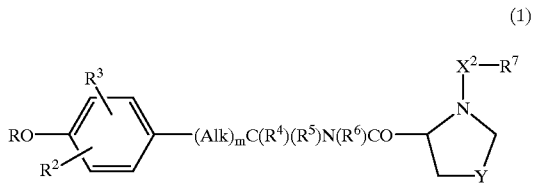

(1)

wherein

R is (1) a group $R^1X^1$— where $R^1$ is an optionally substituted alkyl or aromatic group, and $X^1$ is a covalent bond or a —$(CH_2)_n$—[where n is an integer 1 or 2], —C(O)—, —$CH_2C(O)$—, —NHC(O)—, —$CH_2NHC(O)$—, or —$SO_2$— group, or (2) a group $(Hal^1)_3CSO_2$—, where $Hal^1$ is a fluorine or chlorine atom;

$R^2$ and $R^3$, which may be the same or different, is each a hydrogen or halogen atom or an alkyl, alkoxy, hydroxyl or nitro group;

Alk is an alkylene chain;
m is zero or an integer 1;
$R^4$ is a hydrogen atom or a methyl group;
$R^5$ is a group —$(CH_2)_pCO_2R^8$ where p is zero or an integer 1 and $R^8$ is a hydrogen atom or an alkyl group;
$R^6$ is a hydrogen atom or an alkyl group;
Y is a sulphur atom or a —$S(O)_q$— group where q is an integer 1 or 2;
$X^2$ is a —C(O)—, —C(O)O—, —CONH— or —$S(O)_2$— group;
$R^7$ is an optionally substituted alkyl group or an aryl or aralkyl group;
and the salts, solvates and hydrates thereof.

It will be appreciated that compounds of formula (1) may have one or more chiral centres. Where one or more chiral centres is present, enantiomers or diastereomers may exist, and the invention is to be understood to extend to all such enantiomers, diasteromers and mixtures thereof, including racemates. Formula (1) and the formulae hereinafter are intended to represent all individual isomers and mixtures thereof, unless stated or shown otherwise.

In the compounds of formula (1), when the group $R^1$ is an optionally substituted alkyl group it may be for example an optionally substituted straight or branched chain $C_{1-6}$alkyl group such as an optionally substituted methyl, ethyl, n-propyl, i-propyl, n-butyl, i-butyl, s-butyl or t-butyl group. Optional substituents which may be present on such groups include one, two or three halogen atoms, e.g. fluorine, chlorine, bromine or iodine atoms, or hydroxyl or $C_{1-4}$alkoxy e.g. methoxy or ethoxy groups.

Optionally substituted aromatic groups represented by the group $R^1$ in compounds of formula (1) include for example optionally substituted monocyclic or bicyclic fused ring $C_{6-12}$ aromatic groups, such as optionally substituted phenyl, 1- or 2-naphthyl, 1-or 2-tetrahydronaphthyl, indanyl or indenyl groups.

Optional substituents which may be present on aromatic groups of this type include one, two, three or more substituents selected from halogen atoms, e.g. fluorine, chlorine, bromine or iodine atoms, or $C_{1-6}$alkyl, e.g. methyl or ethyl, $C_{1-6}$alkoxy, e.g. methoxy or ethoxy, hydroxyl, —$NH_2$, —$NHCOCH_3$ or nitro groups. Each of said alkyl or alkoxy groups may be optionally substituted by one, two or three halogen atoms, for example fluorine, chlorine, bromine or iodine atoms, and/or hydroxyl groups. Particular examples of substituted alkyl and alkoxy groups include —$CF_3$, —$OCF_3$, —$CHF_2$, —$OCHF_2$, —$CH_2F$, —$OCH_2F$, —$CH_2OH$, —$(CH_2)_2OH$, —$O(CH_2)_2OH$ and —$C(OH)(CF_3)_2$ groups.

Alkyl groups represented by the groups $R^2$, $R^3$, $R^6$ and/or, when present, $R^8$ in compounds of the invention include for example straight or branched $C_{1-6}$alkyl groups such as methyl, ethyl, n-propyl, i-propyl, n-butyl, i-butyl, s-butyl or t-butyl groups.

Alkoxy groups represented by the groups $R^2$ and/or $R^3$ include straight or branched $C_{1-6}$alkoxy groups such as methoxy or ethoxy groups.

The alkylene chain represented by Alk in compounds of formula (1) may be for example a straight or branched $C_{1-3}$alkylene chain such as a —$CH_2$—, —$(CH_2)_2$— or —$CH(CH_3)$— chain.

Optionally substituted alkyl groups represented by the group $R^7$ in compounds of the invention include optionally substituted straight or branched $C_{1-6}$alkyl groups such as optionally substituted methyl, ethyl, n-propyl, i-propyl, n-butyl, i-butyl, s-butyl or t-butyl groups. Optional substituents which may be present on these groups include one, two or three substituents selected from halogen atoms, e.g. fluorine, chlorine, bromine or iodine atoms, or hydroxyl, $C_{1-4}$alkoxy, e.g. methoxy or ethoxy, —$CO_2H$, amino (—$NH_2$), $C_{1-6}$alkylamino, e.g. methylamino (—$NHCH_3$) or ethylamino, $C_{1-6}$dialkylamino e.g. dimethylamino or diethylamino, —$NHCOCH_3$ or —$NHCO_2R^{10}$ group in which $R^{10}$ is a hydrogen atom or a straight or branched $C_{1-4}$alkyl group such as a methyl, ethyl, i-propyl or t-butyl group.

When in the compounds of the invention the group $R^7$ is an aryl group it may be for example an optionally substituted monocyclic or bicyclic fused ring $C_{6-12}$aromatic group as described above for the group $R^1$.

When in the compounds of formula (1) $R^7$ is an aralkyl group it may be for example an optionally substituted monocyclic or bicyclic fused ring $C_{6-12}$ aromatic $C_{1-3}$alkylene group. In groups of the type the aromatic portion may in particular be an optionally substituted aromatic group as described above for the group $R^1$. The $C_{1-3}$alkylene portion may be for example a methylene or ethylene chain. Particular examples of aralkyl groups include optionally substituted benzyl groups.

The presence of certain substituents in the compounds of formula (1) may enable salts of the compounds to be formed. Suitable salts include pharmaceutically acceptable salts, for example salts derived from inorganic and organic bases. Particular examples of such salts include alkali metal salts such as sodium or potassium salts, alkaline earth metal salts such as magnesium or calcium salts, and organic amine salts such as morpholine, piperidine, dimethylamine or diethylamine salts.

One particular class of compounds according to the invention has the formula (1) wherein $R^4$ is a hydrogen atom and the remaining groups are as defined above for formula (1) and the salts, solvates and hydrates thereof.

In another class of compounds of formula (1) the group $R^5$ is a —$CH_2CO_2H$ group, or in particular is a —$CO_2H$ group.

In compounds of this class, and in general in compounds of formula (1) Y is preferably a sulphur atom.

In another general preference, m in compounds of formula (1) is the integer 1 and Alk in particular is a —$CH_2$— chain. In compounds of this type, and when $R^5$ is a —$CO_2H$ group, the carbon atom to which $R^5$ and Alk are attached forms a chiral centre and is preferably in the L configuration.

The group R in compounds of formula (1) is preferably a $R^1X^1$— group. In compounds of this type $R^1$ is preferably an optionally substituted phenyl group. Particularly useful groups of this type include mono-, di- or trisubstituted phenyl groups. The substituent(s) may be located on any available carbon atom in the phenyl ring at the 2-, 3-, 4-, 5- and 6-positions relative to the point of attachment of the phenyl group to the remainder of the molecule of formula (1). Thus, for example when more than one substituent is present, the substituents may be located at the 2,6- and 2,4,6-positions. Particularly useful substituents include halogen atoms such as chlorine and fluorine atoms. $X^1$ in compounds of these particular types is preferably a —$CH_2$— or —C(O)— group.

$R^6$ in compounds of formula (1) may for example be a methyl group or in particular a hydrogen atom.

$X^2$ in the compounds according to the invention is preferably a —C(O)— group.

The group $R^7$ in the compounds according to the invention may in particular be an optionally substituted $C_{1-3}$alkyl or benzyl group. Optionally substituted $C_{1-3}$alkyl groups are especially useful, and in particular $R^7$ is preferably a methyl group.

Particularly useful compounds according to the invention include:

N-Acetyl-D-thioproline-(O-2,6-dichlorobenzyl)-L-tyrosine;

N-Acetyl-D-thioproline-(O-2,4,6-trichlorobenzyl)-L-tyrosine;

N-Acetyl-D-thioproline-(O-2,6-difluorobenzyl)-L-tyrosine;

N-Acetyl-D-thioproline-(O-2,6-dichlorobenzyl)-3-nitro-L-tyrosine;

N-(3-Carboxy)propionyl-D-thioproline-(O-2,6-dichlorobenzyl)-L-tyrosine;

N-Acetyl-D-thioproline-(O-2,4,6-trichlorobenzoyl)-L-tyrosine and the salts, solvates and hydrates thereof.

Compounds according to the invention are potent and selective inhibitors of the binding of α4 integrins to their ligands. The ability of the compounds to act in this way may be simply determined by employing tests such as those described in the Examples hereinafter.

The compounds are of use in modulating cell adhesion and in particular are of use in the prophylaxis and treatment of diseases or disorders involving inflammation in which the extravasation of leukocytes plays a role. The invention extends to such uses and to the use of each compound for preparing a medicament for treating these diseases and disorders. Particular Diseases or disorders of this type include inflammatory arthritis such as rheumatoid arthritis vasculitis or potydermatomyositis, multiple sclerosis, allograft rejection, diabetes, inflammatory dermatoses such as psoriasis or dermatitis, asthma and inflammatory bowel disease. The compounds may also be useful for modulating the circulating levels of early haematopoichic cells, such as stem cells to enable their collection for e.g. bone marrow transplantation.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection including by bolus injection or infusion or particle mediated injection. Formulations for injection may be presented in unit dosage form, e.g. in glass ampoule or multi dose containers, e.g. glass vials or a device containing a compressed gas such as helium for particle mediated administration. The compositions for bolus injection or infusion may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use. For particle mediated administration the active ingredient may be coated on particles such as microscopic gold particles.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols R, $R^1$–$R^7$, Alk, m, Y and $X^1$ when used in the formulae depicted are to be understood to represent those groups described above in relation to formula (1) unless otherwise indicated. In the reactions described below, it may be necessary to protect reactive functional groups, for example hydroxy or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) wherein $R^5$ is a group —$(CH_2)_p$ $CO_2R^8$ in which p is zero or an integer 1 and $R^8$ is an alkyl group may be prepared by coupling an amine of formula (2):

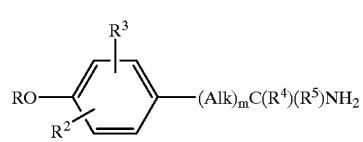
(2)

(where $R^5$ is as just described) or a salt thereof with an acid of formula (3):

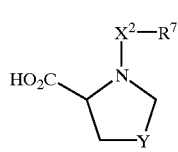
(3)

or an active derivative thereof.

Active derivatives of acids of formula (3) include anhydrides, esters and halides. Particular esters include pentafluorophenyl or succinyl esters.

The coupling reaction may be performed using standard conditions for reactions of this type. Thus for example the reaction may be carried out in a solvent, for example an inert organic solvent such as an amide, e.g. a substituted amide such as dimethylformamide, an ether, e.g. a cyclic ether such as tetrahydrofuran, or a halogenated hydrocarbon, such as dichloromethane, at a low temperature, e.g. around −30° C. to around ambient temperature, optionally in the presence of a base, e.g. an organic base such as an amine, e.g. triethylamine, pyridine, or a cyclic amine, such as N-methylmorpholine.

Where an acid of formula (3) is used, the reaction may additionally be performed in the presence of a condensing agent, for example a diimide such as 1-(3-dimethylaminopropyl)-3-ethylcarbodiimide or N,N'-dicyclohexylcarbodiimide, advantageously in the presence of a catalyst such as a N-hydroxy compound e.g. a N-hydroxytriazole such as 1-hydroxybenzotriazole. Alternatively, the acid may be reacted with a chloroformate, for example ethylchloroformate, prior to reaction with the amine of formula (2).

Intermediate amines of formula (2) wherein $R^5$ is a group —$CO_2R^8$ are either known compounds or may be prepared from known starting materials by methods analogous to those used for the preparation of the known compounds. Where appropriate, standard substitution approaches such as those described below employing for example alkylation, arylation, acylation, halogenation, sulphonylation, nitration or coupling reactions may be used to obtain new R, $R^2$, $R^3$ or $R^5$ substituents in known amines of formula (2). In these reactions the amine may need to be suitably protected, for example as described by Green, T. W. ibid.

Intermediate amines of formula (2) wherein m is zero and $R^5$ is a group —$CH_2CO_2R^8$ may be prepared by reaction of an aldehyde or ketone of formula (4):

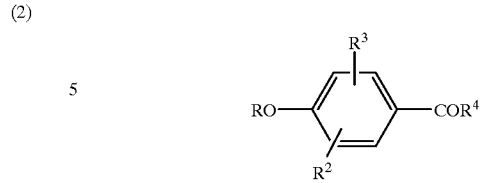
(4)

with malonic acid and ammonia or an ammonium salt, e.g. ammonium acetate, in the presence of a base, followed by reaction with an alcohol $R^8OH$ in the presence of an acid such as hydrochloric acid.

Intermediate amines of formula (2) wherein $R^5$ is a group —$CH_2CO_2R^8$ may be prepared by reaction of an α,β-unsaturated ester of formula (5):

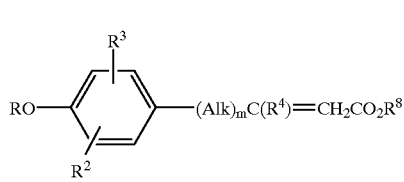
(5)

with benzylamine or a substituted benzylamine, optionally in the presence of a base, followed by hydrogenation using for example hydrogen or a hydrogen donor such as formic acid and a transfer agent such as a metal catalyst, for example palladium on a support such as carbon in a solvent such as methanol at an ambient or elevated temperature.

The esters of formula (5) may be obtained by reaction of an aldehyde or ketone of formula (6):

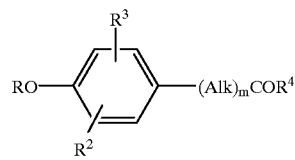
(6)

with a phosphonium salt $(R^9)_3P^+CH_2CO_2R^8Hal^-$ (where Hal is a halogen atom and $R^9$ is for example a phenyl group) or a stabilised ylide $(R^9)_3P=CHCO_2R^8$ in the presence of a base such as sodium ethoxide in a solvent such as ethanol or phenyllithium in a solvent such as tetrahydrofuran at around ambient temperature.

Aldehydes of formula (6) wherein $R^4$ is a hydrogen atom may be prepared by reduction of a corresponding ester of formula (7):

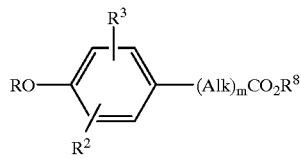
(7)

(where $R^8$ is an alkyl group) using a reducing agent such as a metal hydride, e.g. diisobutylaluminium hydride, at a low temperature e.g. around −78° C. in an organic solvent such as toluene.

Ketones of formula (6) wherein $R^4$ is a methyl group may be prepared by treating a corresponding aldehyde of formula (6) with a Grignard reagent such as methylmagnesium bromide, or methyllithium in a solvent such as tetrahydrofuran, at a low temperature e.g. around −55° C. to 0° C. and oxidising the resulting alcohol using an oxidising agent such as manganese dioxide.

Intermediate aldehydes and ketones of formula (4) and intermediate esters of formula (7) are either known compounds or may be prepared from known starting materials by methods analogous to those used for the preparation of the known compounds, where appropriate employing standard substitution approaches to obtain any desired R, $R^2$, $R^3$ and/or $R^8$ group as described above in relation to the intermediate amines of formula (2).

The acids of formula (3) for use in the preparation of compounds of the invention are also either known compounds or may be prepared from known starting materials by use of analogous processes to those used for the preparation of the known compounds, for example by acylation or sulphonylation of an acid of formula (8):

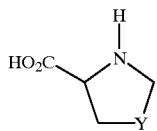

(8)

or a protected derivative thereof using for example a reagent $R^7COHal$, $R^7CO_2H$, $R^7SO_2Hal$ or $R^7NCO$ and standard conditions for reactions of this type such as those described hereinafter for the functionalisation of phenols of formula (9).

In another aspect of the invention a compound of formula (1) may be obtained from a corresponding compound of formula (1) via an inter-conversion process.

Thus, in one particular example, a compound of formula (1) wherein $R^5$ is a —$CO_2H$ or —$CH_2CO_2H$ group may be obtained by hydrolysis of a corresponding ester wherein $R^5$ is a —$CO_2R^8$ or —$CH_2CO_2R^8$ group and $R^78$ is an alkyl group. The hydrolysis may be performed using either an acid or a base depending on the nature of the ester starting material, for example an organic acid such as trifluoroacetic acid or an inorganic base such as lithium hydroxide optionally in an aqueous organic solvent such as an amide, e.g. a substituted amide such as dimethylformamide, an ether, e.g. a cyclic ether such as tetrahydrofuran or dioxane or an alcohol, e.g. methanol at around ambient temperature. Where desired, mixtures of such solvents may be used.

In a still further aspect of the invention a compound of formula (1) may also be prepared by functionalisation of a phenol of formula (9):

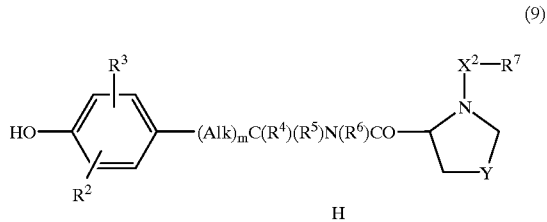

(9)

using standard substitution approaches employing for example alkylation, arylation, acylation, sulphonylation or coupling reactions. In these reactions the starting materials of formula (9) may first be obtained by use of the appropriate phenol intermediates in the reactions previously described to obtain compounds of formula (1).

Thus in one example, a phenol of formula (9) may be alkylated or arylated using a reagent $R^1X^1L$ in which $X^1$ is a covalent bond or a —$(CH_2)_n$ group and L is a leaving atom or group such as a halogen atom, e.g. a fluorine, bromine, iodine or chlorine atom or a sulphonyloxy group such as an alkylsulphonyloxy, e.g. trifluoromethylsulphonyloxy or arylsulphonyloxy, e.g. p-toluenesulphonyloxy group.

The alkylation or arylation reaction may be carried out in the presence of a base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran at for example around 0° C. to around ambient temperature. The compounds $R^1X^1L$ are either known and readily available or may be obtained by simple manipulation of known compounds, for example as described in the Examples hereinafter.

In another example, a phenol of formula (9) may be functionalised by acylation, for example by reaction with a reagent $R^1X^1Hal$— [wherein $X^1$ is a —C(O)—, —$CH_2C$(O)— or —NHC(O)— group and Hal is a halogen atom such as a chlorine atom] in the presence of a base, such as a tertiary amine, e.g. triethylamine, in a solvent such as a halogenated hydrocarbon, e.g. dichloromethane or carbon tetrachloride, at for example ambient temperature.

In a further example a compound of the invention may be obtained by sulphonylation of a phenol of formula (9) by reaction with a reagent $R^1X^1L$ or $(Hal^1)_3CSO_2L$ [in which $X^1$ is —$SO_2$— and L is a leaving group as defined above] in the presence of a base, for example an inorganic base such as sodium hydride in a solvent such as an amide, e.g. a substituted amide such as dimethylformamide at for example ambient temperature.

In another example a compound of formula (1) wherein R is a group $R^1X^1$ [where $X^1$ is a covalent bond or a —$(CH_2)_n$ group] may be obtained by coupling a phenol of formula (9) with a reagent $R^1OH$ or $R^1$ $(CH_2)_nOH$ in a solvent such as tetrahydrofuran in the presence of a phosphine, e.g. triphenylphosphine and an activator such as diethyl-, diisopropyl- or dimethylazodicarboxylate.

In a further process according to the invention a compound of formula (1) may be prepared by acylation or sulphonylation of an intermediate of formula (10):

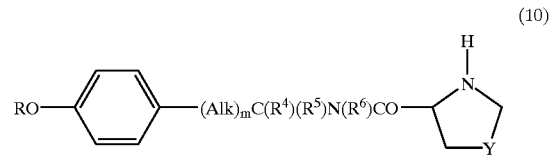

(10)

Reagents for these reactions include for example compounds of the types $R^7COHal$, $R^7CO_2H$, $R^7SO_2Hal$ or $R^7NCO$. The reactions may be performed using standard conditions such as those described above in relation to the acylation or sulphonylation of phenols of formula (9). It will be appreciated that in some instances and under suitable conditions the reaction may also be performed on compounds of formula (10) in which R is a hydrogen atom so that acylation or sulphonylation takes place at both ends of the molecule. In general in this process any carboxyl group in intermediates of formula (10) will need to be protected, for example as a methyl ester, and, where required, the free acid subsequently regenerated by hydrolysis as described herein.

Salts of compounds of formula (1) may be prepared by reaction of a compound of formula (1) with an appropriate base in a suitable solvent or mixture of solvents e.g. an organic solvent such as an ether e.g. diethylether, or an alcohol, e.g. ethanol using conventional procedures.

Where it is desired to obtain a particular enantiomer of a compound of formula (1) this may be produced from a corresponding mixture of enantiomers using any suitable conventional procedure for resolving enantiomers.

Thus for example diastereomeric derivatives, e.g. salts, may be produced by reaction of a mixture of enantiomers of formula (1) e.g. a racemate, and an appropriate chiral compound, e.g. a chiral base. The diastereomers may then be separated by any convenient means, for example by crystallisation and the desired enantiomer recovered, e.g. by treatment with an acid in the instance where the diastereomer is a salt.

In another resolution process a racemate of formula (1) may be separated using chiral High Performance Liquid Chromatography. Alternatively, if desired a particular enantiomer may be obtained by using an appropriate chiral intermediate in one of the processes described above.

The following Examples illustrate the invention. All temperatures are in °C. The following abbreviations are used:

| | |
|---|---|
| EDC - 1-(3-dimethylaminopropyl)-3-ethylcarbodiimide; | DMSO - dimethylsulphoxide; |
| DMF - dimethylformamide; | THF - tetrahydrofuran; |
| HOBT - 1-hydroxybenzotriazole; | NMM - N-methyl-morpholine; |
| TFA - trifluoroacetic acid; | Ph - phenyl; |
| DCM - dichloromethane; | Ar - aryl; |
| tyr - tyrosine; | pyr - pyridine; |
| thiopro - thioproline; | Bu - butyl; |
| Me - methyl; | |
| BOC - t-butoxycarbonyl. | |

Intermediate 1
N-Acetyl-D-thioproline-L-tyrosine tert.butyl ester

EDC (4.22 g, 22 mmol) was added to a solution of N-acetyl-D-thioproline (3.50 g, 20 mmol), tyrosine tert.butyl ester (4.74 g, 20 mmol), HOBT (2.97 g, 22 mmol) and NMM (2.42 ml, 22 mmol) in DMF (80 ml) at 0°. The mixture was stirred at room temperature overnight. The DMF was evaporated in vacuo and the residue dissolved in ethyl acetate (600 ml) and water (50 ml). The organic phase was washed with 10% citric acid (150 ml), saturated aqueous NaHCO$_3$ (150 ml), water (150 ml) and brine (150 ml), dried (Na$_2$SO$_4$) and evaporated in vacuo to give the title compound as an off-white solid (7.39 g, 94%); δH (DMSO-d$_6$, 300K) (2 rotameric species observed) 9.17 (1H, br s, ArCH), 8.43 (3, J 8.0 Hz), and 8.09 (d, J 8.0 Hz) together (1H, CONH), 6.98 (2H, t, J 7.6, ArH), 6.64 (2H, d, J 7.3, ArH), 4.81–4.67 (m), 4.47 (d, J 8.7 Hz) and 4.35–4.21 (m), together (4H, CHα-tyr, CHαthiopro and NCH$_2$S), 3.32 (dd, J 7.2, 11.6 Hz), 3.17 (dd, J 7.5, 11.6 Hz), 2.99–2.72 (m) together (4H, CH$_2$Ar+CHCH$_2$S), 2.06 (s) and 1.84 (s) together (3H, CH$_3$CO) and 1.36 (9H, S, CO$_2$$^t$Bu); m/z (ESI, 15V) 395 (M$^+$+1).

Intermediate 2
N-Acetyl-D-thioproline-L-tyrosine methyl ester

EDC (2.11 g, 11 mmol) was added to a stirred solution of N-acetyl-D-thioproline (1.75 g, 10 mmol), tyrosine methyl ester (2.32 g, 10 mmol), HOBT (1.49 g, 11 mmol) and NMM (2.31 ml, 21 mmol) in DMF (50 ml) at 0°. The mixture was stirred at room temperature overnight. The DMF was evaporated in vacuo and the residue dissolved in ethyl acetate (400 ml), and water (50 ml). The organic phase was washed with 10% citric acid (100 ml), saturated aqueous NaHCO$_3$ (100 ml), water (100 ml) and brine (100 ml), dried (Na$_2$SO$_4$) and evaporated in vacuo to give the title compound as a slightly yellow powdery solid (2.75 g, 78%), used without further purification. A small portion was crystallised from EtOAC to give a white microcrystalline solid, m.p. 189–190°. δH (DMSO-D$_6$, 400K) 7.7 (1H, br s, CONH), 6.98 (2H, d, J 8.6 Hz, ArH), 6.69 (2H, d, J 8.5 Hz, ArH), 4.83 (1H, dd, J 3.9, 7.4 Hz, CHαthiopro), 4.77 (1H, d, J 9.2 NCH$_A$H$_B$S), 4.53 (1H, dt, J 5.8, 8.1 Hz, CHαtyr), 4.38 (1H, d, J 9.2 Hz, NCH$_A$H$_B$S), 3.65 (3H, s, C O$_2$HC), 3.25 (1H, dd, J 7.3, 11.5 Hz, CHCH$_A$H$_B$S), 3.05–2.97 (2H, m, CH$_A$H$_B$Ar+ CHCH$_A$H$_B$S), 2.89 (1H, dd, J 8.2, 14.1 Hz, CH$_A$H$_B$Ar) and 1.99 (3H, s, CH$_3$CO) [phenolic OH not observed at 400K, for δH (DMSO-d$_6$, 300K) 9.19 (1H, br s, ArOH)]; m/z ESI, 27V), 353 (M$^+$+1).

Intermediate 3
3-Nitro-L-tyrosine methyl ester hydrochloride

Acetyl chloride (8.9 ml, 125 mmol) was added slowly to methanol (100 ml) at 0°. 3-Nitro-L-tyrosine (5.65 g, 25 mmol) was added and the mixture refluxed for 2 h. The solvent was evaporated in vacuo and the yellow solid obtained recrystallised from methanol to give the title compound as yellow needles (2.97 g, 43%), m.p. 200–201°. (Found: C, 43.29;H, 4.69; N, 10.19. C$_{10}$H$_{12}$N$_2$O$_5$HCl requires C, 43.41;H, 4.74; N, 10.13%); δH (CD$_3$OD) 8.00 (1H, d, J 2.2 Hz, ArH), 7.53 (1H, dd, J 2.3, 8.6 Hz, ArH), 7.17 (1H, d, J 8.6 Hz, ArH), 4.37 (1H, dd, J 6.4, 7.0 Hz, CH$_α$), 3.83 (3H, s, CO$_2$CH$_3$), 3.29 (1H, dd, J 6.3, 14.6 Hz, CH$_A$H$_B$Ar) and 3.20 (1H, dd, J 7.1, 14.6 Hz, CH$_A$H$_B$Ar); m/z (ES, 27V) 241 (M$^+$+1).

Intermediate 4
N-Acetyl-D-thioproline-3-nitro-L-tyrosine methyl ester

EDC.HCl (1.056 g, 5.5 mmol) was added to a solution of N-acetyl-D-thioproline (875 mg, 5 mmol), Intermediate 3 (1.38 g, 5 mmol), HOBT (743 mg, 5.5 mmol) and NMM (1.15 ml, 10.5 mmol) in DMF (25 ml) at room temperature. The reaction mixture was stirred overnight. The DMF was evaporated in vacuo and the residue dissolved in ethyl acetate (150 ml) and water (50 ml). The organic phase was washed with hydrochloric acid (1M, 30 ml), saturated aqueous NaHCO$_3$ (30 ml), water (50 ml) and brine (30 ml), dried (Na$_2$SO$_4$) and evaporated in vacuo to give the title compound as a yellow foam (1.59 g, 80%); δH (DMSO-d$_6$, 300K) (2 rotameric species observed) 10.79 (s) and 10.76 (s) together (1H, ArOH), 8.61 (d, J 8.2 Hz) and 8.32 (d, J 8.3 Hz) togther (1H, CONH), 7.75–7.71 (1H, m, ArH), 7.44–7.37 (1H, m, ArH), 7.06–7.01 (1H, m, ArH), 4.74–4.67 (m) and 4.56–4.43 (m) and 4.44 (d, J 8.6 Hz), and 4.19 (d, J 9.7 Hz) together (4H, 2×CH$_α$+NCH$_2$S), 3.64 (3H, s, CO$_2$CH$_3$), 3.33–2.77 (4H, m, CHCH$_2$S+CH$_2$Ar) and 2.03 (s) and 1.84 (s) together (3H, CH$_3$CO); m/z (ES, 30V) 398 (M$^+$+1).

Intermediate 5
α-Methyl-L-tyrosine methyl ester hydrochloride

Anhydrous hydrogen chloride was bubbled through a solution of α-methyl-L-tyrosine (1 g, 5.13 mmol) in methanol (100 ml) for a few minutes and the solution stirred at room temeprature for 48 h. The solvent was evaporated in vacuo and the residue freeze dried from a mixture of methanol and water to give the title compound as a white powder (1.28 g, 100%); δH (CD$_3$OD) 7.00 (2H, d, J 8.6 Hz, ArH), 6.78 (2H, d, J 8.6 Hz, ArH), 3.82 (3H, s, CO$_2$CH$_3$), 3.19 (1H, d, J 14.3 Hz, CH$_A$H$_B$Ar), 3.01 (1H, d, J 14.3 Hz, CH$_A$H$_B$Ar) and 1.59 (3H, s, CCH$_3$); m/z (ES, 27V) 210 (M$^+$+1).

Intermediate 6
N-Acetyl-D-thioproline-α-methyl-L-tyrosine methyl ester

EDC.HCl (760 mg, 3.96 mmol) was added to a solution of N-acetyl-D-thioproline (630 mg, 3.6 mmol), Intermediate 5 (880 mg, 3.6 mmol), HOBT (535 mg, 3.96 mmol) and NMM (834 μl, 7.6 mmol) in DMF (20 ml). The mixture was stirred at room temperature overnight. The DMF was evaporated in vacuo and the residue dissolved in ethyl acetate (150 ml) and water (50 ml). The organic phase was washed with 10% citric acid (50 ml), saturated aqueous NaHCO$_3$ (50 ml) and water (50 ml), dried (Na$_2$SO$_4$) and evaporated in vacuo. The residue was purified by column chromatography (SiO$_2$, methanol/DCM, 7:93) to give the title compound as a colourless gum (680 mg, 52%); δH (DMSO-d$_6$, 400K) 7.40 (1H, br s, CONH), 6.93 (2H, d, J 8.6 Hz, ArH), 6.68 (2H, d, J 8.3 Hz, ArH), 4.84 (1H, dd, J 3.8, 7.4 Hz, CHαthiopro), 4.78 (1H, d, J 9.2 Hz, NCH$_A$H$_B$S), 4.40 (1H, d, J 9.2 Hz, NCH$_A$H$_B$S), 3.63 (3H, S, CO$_2$CH$_3$), 3.30 (1H, dd, J 7.4, 11.5 Hz, CHCH$_A$H$_B$S), 3.16 (1H, dd, J 3.8, 11.5 Hz, CHCH$_A$H$_B$S), 3.13 (1H, d, J 13.7 Hz, CH$_A$H$_B$Ar), 3.03 (1H, d, J 13.7 Hz, CH$_A$H$_B$Ar), 2.02 (3H, s, CH$_3$CO) and 1.38 (3H, s, CCH$_3$); m/z (ES, 15V) 367 (M$^+$+1).

Intermediate 7
2,4,6-Trichlorobenzyl alcohol

A solution of lithium aluminium hydride (1M in THF, 18 mmol, 18 ml) was added slowly to a solution of 2,4,6-trichlorobenzoyl chloride (4.35 g, 17.8 mmol) in THF (70 ml) at 0°. After 1 h water (685 μl) was added, followed by aqueous sodium hydroxide (3M, 685 μl) and more water (2.06 ml). The suspension was stirred vigorously for 1 h, the precipitate filtered off and the filtrate evaporated in vacuo to give a slightly yellow solid. Recrystallisation from diisopropylether gave the title compound as white needles (2.63 g, 70%), m.p. 100–101° δH (CDCl$_3$) 7.35 (2H, s, ArH), 4.91 (2H, br s, CH$_2$CH) and 2.07 (1H, br s, CH); m/z (ES, 60V) 193 (M—OH).

Intermediate 8
2,4,6-Trichlorobenzyl bromide

Thionyl bromide (682 μl, 8.8 mmol) was added to a solution of Intermediate 7 (846 mg, 4 mmol) in DCM (20 ml) at 0°. The reaction was stirred at room temperature overnight then quenched with water. The mixture was diluted with DCM (100 ml), washed with saturated aqueous NaHCO$_3$ (30 ml) and water (30 ml), dried (Na$_2$SO$_4$) and evaporated in vacuo. The residue was purified by column chromatography (short plug SiO$_2$, hexane) to give the title compound as a colourless oil which crystallised on standing to white crystals (982 mg, 89%), m.p. 51–52°. δH (CDCl$_3$) 7.36 (2H, s, ArH) and 4.70 (2H, s, CH$_2$Br).

Intermediate 9
N-Boc-D-thioproline-(O-benzyl)-L-tyrosine methyl ester

NMM (1.73 g, 1.9 ml, 17.13 mmol), HOBT (2.53 g, 18.74 mmol) N-Boc-D-thioproline (4.0 g, 17.17 mmol) and EDC (3.30 g, 17.19 mmol) were added sequentially to a stirred solution of O-benzyl-L-tyrosine methyl ester hydrochloride (5.02 g, 15.59 mmol) in dry DMF (50 ml). The reaction mixture was stirred at room temperature under N$_2$ for 3 h. The DMF was removed in vacuo and the residue partitioned between EtOAc (150 ml) and 5% aqueous Na$_2$CO$_3$ (50 ml). The phases were separated and the aqueous phase re-extracted with EtOAc (2×50 ml). The combined organic extracts were washed consecutively with 5% aqueous hydrochloric acid (30 ml), 5% aqueous Na$_2$CO$_3$ (30 ml) and brine (20 ml) then dried (Na$_2$SO$_4$) and evaporated in vacuo to afford the title compound as a straw coloured oil (7.8 g). This was used without further purification but can be purified by flash chromatography (SiO$_2$; 2% MeOH/DCM). δH (DMSO-d$_6$), 7.48–7.28 (5H, m, PhH), 7.03 (2H, d, J 8.6 Hz, ArH), 6.88 (2H, d, J 8.6 Hz, ArH), 6.82 (1H, br s NHCO), 5.02 (2H, s, PhCH$_2$O), 4.81 (1H, apparent, dt, J 5.8 Hz, CHα-tyr), 4.64 (1H, br d J 9 Hz, NCH$_{AB}$S), 4.25 (1H, d, J 9.2 Hz, NCH$_A$H$_B$S), 3.69 (3H, s, CO$_2$CH$_3$), 3.34 (1H, br d, J 11 Hz, CHCH$_A$H$_B$S), 3.13 (1H, brd J~7, ~11 Hz, CHCH$_A$H$_B$S) 3.06 (1H, d, J 5.8 Hz, CH$_2$Ar) and 1.45 (9H, s CO$_2$tBu); m/z (ESI, 15V) 523 (MNa$^+$, 55), 501 (MH$^+$, 74, 445 (100).

Intermediate 10
D-Thioproline-(O-benzyl)-L-tyrosine methyl ester

Intermediate 9 (8.2 g) was stirred in trifluoroacetic acid (50 ml) and DCM (50 ml) at room temperature for 1 h. The solvent was removed in vacuo and the residue partitioned between EtOAc (150 ml) and saturated aqueous NaHCO$_3$ (50 ml). The phases were separated and the aqueous phase re-extracted with EtOAc (32×50 ml). The combined organic extracts were washed with brine (30 ml), dried (Na$_2$SO$_4$) and evaporated in vacuo. The obtained solid was treated with diethyl ether (50 ml) and filtered off with a little ether washing affording the title compound as white needles (5.3 g, 8.1%): m.p. 138–140°. (Found C, 62.88;H, 6.06; N, 6.92. C$_{21}$H$_{24}$N$_2$O$_4$S requires C, 62.98;H, 6.04; N, 7.00%); δH (50% CDCl$_3$/CD$_3$OD) 7.42–7.23 (5H, m, PhH), 7.03 (2H, d, J 8 Hz, ArH), 6.86 (2H, d, J 8.7 Hz, ArH), 5.02 (2H, s, OCH$_2$Ph), 4.68 (1H, dd, J 7.5, 5.5 Hz, CHα-tyr), 4.10 (1H, d, J 9.6 Hz, NCH$_A$H$_B$S), 3.96 (1H, d, J 9.6 Hz, NCH$_A$H$_B$S), 3.96–3.94 (1H, m, CHα-thiopro), 3.69 (3H, s, CO$_2$CH$_3$), 3.13–3.04 (2H, m) and 3.01–2.92 (2H, m) together (4H, CHCH$_2$S and CH$_2$Ar). m/z (ESI, 27V) 401 (MH$^+$, 100).

EXAMPLE 1
N-Acetyl-D-thioproline-(O-2,6-dichlorobenzoyl)-L-tyrosine tert.butyl ester A solution of Intermediate 1 (705 mg, 1.79 mmol) in THF (5 ml) was added to a suspension of sodium hydride (60% in oil, 79 mg, 1.97 mmol) and 2,6-dichlorobenzoyl chloride (283 μl, 1.97 mmol) in THF (10 ml) at 0°. The mixture was stirred at room temperature for 6 h then quenched with aqueous NH$_4$Cl (5 ml). The mixture was extracted with DCM (2×75 ml) and the combined organic extracts dried (Na$_2$SO$_4$) and evaporated in vacuo. The residue was purified by chromatography (SiO$_2$; ethyl acetate/hexane 80:20) to give the title compound as a white foam (920 mg, 91%); δH (DMSO-d$_6$, 300K) (2 rotomeric species observed) 8.55 (d, J 7.9 Hz), and 8.25 (d, J 8.0 Hz), togther (1H, NHCO), 7.70–7.59 (3H, m, COArH), 7.38–7.34 (2H, m, CH$_2$ArH), 7.21–7.17 (2H, m, CH$_2$ArH), 4.80–4.67 (m) and 4.50–4.34 (m) and 4.48 (d, J 8.7 Hz) and 4.23 (d, J 9.6 Hz) together (4H, 2×CHα+NCH$_2$S), 3.30–2.80 (4H, m, CH$_2$Ar+ CHCH$_2$S), 2.07 (s) and 1.83 (s) together (3H, CH$_3$CO) and 1.38 (9H, s, CO$_2$tBu); m/z (ESI, 15V) 567 (M$^+$+1).

EXAMPLE 2
N-Acetyl-D-thioproline-(O-2,6-dichlorobenzoyl) L-tyrosine

A solution of the compound of Example 1 (910 mg, 1.60 mmol) in a mixture of TFA/H$_2$O (9:1, 20 ml) was stirred at room temperature for 2 h. The solvents were evaporated in vacuo and the residue freeze dried from a mixture of methanol/H$_2$O to give the title compound as a fluffy white solid (809 mg, 99%) δH (DMSO-d$_6$, 400K) 7.75 (1H, br d, CONH), 7.62–7.53 (3H, m, COArH), 7.34 (2H, d, J 8.7 Hz), CH$_2$-ArH), 7.20 (2H, d, J 8.7 Hz, CH$_2$ArH), 4.82 (1H, dd, J 3.9, 7.3 Hz, CHαthiopro), 4.76 (1H, d, J 9.2 Hz CH$_A$H$_B$S), 4.57 (1H, dt, J 5.4, 8.4 Hz, CHαtyr), 4.37 (1H, d, J 9.1 Hz, NCH$_A$H$_B$S), 3.25 (1H, dd, J 7.4, 11.6 Hz, CHCH$_A$H$_B$S), 3.19 (1H, dd, J 5.3, 14.1 Hz, CH$_A$H$_B$Ar), 4.07–2.99 (2H, m, CHCH$_A$H$_B$S+CH$_A$H$_B$Ar) and 1.98 (3H, s, CH$_3$CO); m/z (ESI, 27V) 511 M$^+$+1); [α]$_D^{24.5}$=+76.53° (c, =0.69, methanol).

EXAMPLE 3
N-Acetyl-D-thioproline-(O-2,6-dimethoxybenzoyl)-L-tyrosine methyl ester A solution of Intermediate 2 (352 mg, 1 mmol) in DMF (5 ml) was added to a suspension of sodium hydride (60% in oil, 44 mg, 1.1 mmol) in DMF (3 ml) at 0°. After 5 min at room temperature a yellow solution was obtained, to this was added a solution of 2,6-dimethoxybenzoyl chloride (241 mg, 1.22 mmol) in DMF (2 ml). The mixture was stirred for 1 h then quenched with water and the DMF evaporated in vacuo. The residue was dissolved in ethyl acetate (100 ml) and washed in water (3×30 ml) and brine (30 ml), dried ($Na_2SO_4$) and evaporated in vacuo. The residue was purified by chromatography ($SiO_2$, DCM/methanol, 95:5) to give the title compound as a yellow gum (462 mg, 90%); δH (DMSO-$D_6$, 300K) (2 rotameric species observed) 8.63 (3, J 8.2 Hz) and 8.38 (d, J 8/1 Hz) toget her (1H, CONH), 7.43 (1H, t, J 8.4 Hz, CO-Ar$_p$H), 7.29 (2H, t, J 8.1 Hz), $CH_2$ArH), 7.09–7.06 (2H, m, $CH_2$ArH), 6.77 (2H, d, J 8.4 Hz, CO-ArmH), 4.79–4.68 (m) and 4.60–4.44 (m) and 4.45 (d, J 8.7 Hz) and 4.23 (d, J 9.7 Hz) together (4H, 2×CHα+NCH$_2$S), 3.84 (6H, s, 2×ArOMe), 3.65 (s) and 3.64 (s) together (3H, $CO_2$Me), 3.32–2.73 (4H, m, $CH_2$Ar+CHCH$_2$S) and 2.06 (s) and 1.84 (s) together (3H, $CH_3$CO); m/z (ESI, 15V) 517 ($M^+$+1).

EXAMPLE 4

N-Acetyl-D-thioproline-(O-2,6-dimethoxybenzoyl)-L-tyrosine

Lithium hydroxide (41 mg, 0.97 mmol) was added to a solution of the compound of Example 3 (455 mg, 0.88 mmol) in a mixture of THF (10 ml) and water (10 ml). The mixture was stirred at room temperature for 10 min then the THF was evaporated in vacuo. The residue was purified by chromatography ($SiO_2$; DCM/methanol/acetic acid, 90:5:5). The gum obtained was freeze-dried from a mixture of methanol and water to give the title compound as a fluffy white solid (401 mg, 91%). δH (DMSO-$d_6$, 400K) 7.7 (1H, br d, CONH), 7.40 (1H, t, J 8.4 Hz, COAr$_p$H), 7.28 (2H, d, J 8.7 Hz, $CH_2$ArH), 7.09 (2H, d, J 8.6 Hz, $CH_2$ArH), 6.77 (2H, d, J 7.8 Hz, COAr$_m$H), 4.83 (1H, dd, J 4.0, 7.3 Hz, CHαthiopro), 4.77 (1H, d, J 9.2 Hz, NCH$_A$H$_B$S), 4.57–4.51 (1H, m, CHαtyr), 4.38 (1H, d, J 98.2 Hz, NCH$_A$H$_B$S), 3.87 (6H, s, 2×CArOMe), 3.25 (1H, dd, J 7.4, 11.5 Hz, CHCH$_A$H$_B$S), 3.17 (1H, dd, J 5.4, 14.1 CH$_A$H$_B$Ar), 3.06–2.98 (2H, m, CHCH$_A$H$_B$S+CH$_A$H$_B$Ar) and 1.99 (3H, s, $CH_3$CO), m/z (ESI, 15V) 503 ($M^+$+1).

EXAMPLE 5

N-Acetyl-D-thioproline-(O-benzyl)-L-tyrosine methyl ester

EDC (211 mg, 1.1 mmol) was added to a stirred solution of N-acetyl-D-thioproline (175 mg, 1 mmol), O-benzyl tyrosine methyl ester hydrochloride (322 mg, 1 mmol), HOBT (149 mg, 1.1 mmol) and NMM (242 µl, 2.2 mmol) in DCM (10 ml) at 0°. The mixture was stirred at room temperature overnight then diluted with DCM (100 ml). The DCM solution was washed with 1M hydrochloric acid (30 ml), saturated aqueous NaHCO$_3$ (30 ml) and water (30 ml), dried ($Na_2SO_4$) and evaporated in vacuo. The residue was purified by chromatography ($SiO_2$; ethyl acetate) to give the title compound as a white foam (417 mg, 94%); δH (DMSO-$d_6$, 300K) (2 rotameric species observed) 8.55 (d. J 7.8 Hz) and 8.28 (3, J 8.1 Hz) together (1H, NHCO), 7.43–7.25 (5H, m, Ph), 7.14–7.08 (2H, m, ArH), 6.92–6.88 (2H, m, ArH), 5.06 (2H, s, $CH_2$Ph), 4.79–4.66 (m) and 4.45–4.42 (m) and 4.21 (d, J 9.7 Hz) together (4H, CHα-tyr, CHα-thiopro and NCH$_2$S), 3.62 (s) and 3.61 (s) together (3H, $CO_2$Me), 3.28–2.71 (4H, m, CHCH$_2$Ar+CHCH$_2$S) and 2.04 (s) and 1.82 (s) togher (3H, $CH_3$CO); m/z (ESI, 15V) 443 ($M^+$+1).

The following compounds were prepared in a similar manner using the appropriate tyrosine esters:

N-Acetyl-D-thioproline-(O-benzyl)-L-tyrosine tert.butyl ester

δH (DMSO-$d^6$ 400K), 7.64 (1H, br d, CONH), 7.43–7.30 (5H, m, Ph), 7.12 (2H, d, J 8.8 Hz, ArH), 6.92 (2H, d, J 8.7 Hz, ArH), 5.09 (2H, s, OCH$_2$Ph), 4.82 (1H, dd, J 7.3, 3.8 Hz, CHαthiopro), 4.77 (1H, d, J 9.2 Hz, NCH$_A$H$_B$S), 4.43 (1H, dt, J 8.1, 6.0 Hz, CHαtyr), 4.37 (1H, d, J 9.2 Hz, NCH$_A$H$_B$S), 3.25 (1H, dd, J 11.5, 7.4 Hz, CHCH$_A$H$_B$S), 3,03 (1H, dd, J 11.5, 3.8 Hz, CHCH$_A$H$_B$S), 3.02 (1H, dd, J 14.2, 6.2 Hz, CHCH$_A$H$_B$Ar), 2.91 (1H, dd, J 14.2, 8.1 Hz, CHCH$_A$H$_B$Ar), 1.99 (3H, s, COCH$_3$) and 1.40 (9H, s, $CO_2$tBu) (acid proton not observed at 400K); m/z (ESI, 15V) 485 ($M^+$+1).

N-Acetyl-D-thioproline-(O-benzyl)-L-tyrosine ethyl ester

δH (DMSO-$d^6$ 390K), 7.73(1H, br s, NH), 7.44–7.30 (5H, m, Ph-H), 7.12 (2H, ABd, J 8.7 Hz, Ar-H), 6.92 (2H, m, Ar-H), 5.09 (2H, s, $CH_2$OAr), 4,79 (2H, m, CHαthiopro +NCH$_A$H$_B$S), 4.53 (1H, m, CHαtyr), 4.36 (1H, m, NCH$_A$H$_B$S), 4.10 (2H, Q, J 7.1 Hz, $CH_2CH_3$), 3.31–2.88 (4H, m, CHCH$_2$S+CHCH$_2$Ar), 1.98 (s) and 1.95 (s) together (3H, MeCO) and 1.18 (3H, t, J 7.1 Hz, $CH_2CH_3$); m/2 (ESI, 60V) 457 ($M^+$+1).

EXAMPLE 6

N-Acetyl-D-thioproline-(O-benzyl)-L-tyrosine

Lithium hydroxide (47 mg, 1.1 mmol) was added to a solution of the compound of Example 5 (410 mg, 0.93 mmol) in a mixture of THF (10 ml) and water 10 ml). The mixture was stirred for 30 min at room temprature then the THF was evaporated in vacuo. The aqueous residue was acidified (1M hydrochloric acid and extracted with DCM (2×50 ml). The combined organic extracts were dried ($Na_2SO_4$) and evaporated in vacuo to give, a gummy solid. This was dissolved in methanol, diluted with water and freeze-dried to give the title compound as a fluffy white solid (369 mg, 93%). δH (DMSO-$d_6$, 400K) 7.65 (1H, br d, CONH), 7.43–7.29 (5H, m, Ph), 7.12 (2H, d, J 8.5 Hz, ArH), 6.91 (2H, d, J 8.6, ArH), 5.08 (2H, s, $CH_2$Ph), 4.81 (1H, dd, J 3.9–7.4 Hz, CHα-thiopro), 4.76 (1H, d, J 9.2 Hz, NCH$_A$H$_B$S), 4.50 (1H, dt, J 5.4, 8.3 Hz, CHαtyr), 4.36 (1H, d, J 9.1 Hz, NCH$_A$H$_B$S), 3.23 (1H, dd, J 7.1, 11.5 Hz, CHCH$_A$H$_B$S), 3.07 (1H, dd, J 5.4, 14.1 Hz, CH$_A$H$_B$Ar), 2.99 (1H, dd, J 3.9, 11.5 Hz, CHCH$_A$H$_B$S), 2.91 (1H, dd, J 8.4, 14.2 Hz, CH$_A$H$_B$Ar) and 1.97 (3H, s, $CH_3$CO) [COOH not observed at 400K. δH (DMSO-$d_6$, 300K) 12.7 1 Hv. br S. $CO_2$H]; m/z (ESI, 15V) 429 ($M^+$+1).

EXAMPLE 7

N-Acetyl-D-thioproline-(O-2,6-dicholorobenzyl)-L-tyrosine methyl ester

A solution of Intermediate 2 (352 mg, 1 mmol) in DMF (5 ml) was added to a suspension of sodium hydride (60% in mineral oil, 44 mg, 1.1 mmol) in DMF (3 ml) at room temperature. After 5 min a solution of 2,6 dichlorobenzyl bromide (288 mg, 1.2 mmol) in DMF (2 ml) was added and the mixture stirred for 90 min. The reaction was quenched with a few drops of water and the DMF was removed in vacuo. The residue was dissolved in ethyl acetate (100 ml), washed with water (2×50 ml) and brine (25 ml), dried ($Na_2SO_4$) and evaporated in vacuo. The residue was purified by column chromatorgaphy ($SiO_2$; methanol/DCM 5:95) to give the title compound as a white foam (499 mg, 97%); δH (DMSO-$d_6$, 300K) (2 rotameric species observed) 8.57 (d, J 8.2 Hz) and 8.31 (d, J 8.1 Hz), together (1H, NHCO), 7.57–7.43 (3H, m, OCH$_2$ArH), 7.18–7.12 (2H, t, J 8.1 Hz, CHCH$_2$ArH), 6.98–6.94 (2H, m, CHCH$_2$ArH), 5.19 (2H, s, OCH$_2$Ar), 4.79–4.68 (m) and 4.50–4.44 (m) and 4.45 (d, J 8.8 Hz), and 4.23 (d, J 9.7 Hz) together (4H, 2×CH$_α$+NCH$_2$S), 3.64 (s) and 3.635 (s) together (3H, $CO_2CH_3$), 3.35–3.27 (m) and 3.17–2.49 (m) together (4H, CHCH$_2$Ar+CHCH$_2$S) and 2.05 (s) and 1.83 (s) together (3H, CH$_3$CON); m/z (ESI, 15V) 511 (M$^+$+1).

The following compound was prepared in a similar manner:

N-Acetyl-D-thioproline-(O-2,6-dichlorobenzyl)-L-tyrosine ethyl ester

δH (DMSO-d$^6$, 390K) 7.51 (1H, br d, J 2.0 Hz, NH), 7.48–7.41 (3H, m, Cl$_2$-Ar-H), 7.14 (2H, d, J 8.6 Hz, Ar-H), 6.96 (2H, d, J 8.6 Hz, Ar-H), 5.26 (2H, s, CH$_2$OAr), 4.81 (1H, m, CHα-thiopro), 4.76 (1H, d, J 9.2 Hz, NCH$_A$H$_B$S), 4.53 (1H, m, CHαtyr), 4.38 (1H, d, J 9.2 Hz, NCH$_A$H$_B$S), 4.11 (2H, q, J 7.1 Hz, CH$_2$CH$_3$), 3.24–2.99 (4H, m, CHCH$_2$S+CHCH$_2$Ar), 1.99 (3H, s, COMe) and 1.19 (3H, t, J 7.1 Hz, CH$_2$CH$_3$). m/z (ESI, 60V), 527,525 (M$^+$+1).

EXAMPLE 8
N-Acetyl-D-thioproline-(O-2,6-dichlorobenzyl)-L-tyrosine

Lithium hydroxide (44 mg, 1.05 mmol) was added to a solution of the compound of Example 7 (490 mg, 0.959 mmol) in a mixture of THF (10 ml) and water, (10 ml). The mixture was stirred at room temperature for 15 min then the THF was evaporated in vacuo. The aqueous residue was acidified (1M hydrochloric acid) and extracted with DCM (2×50 ml). The combined extracts were dried (Na$_2$SO$_4$) and evaporated in vacuo to give the title compound as a white solid (464 mg, 97%) (Found: C, 53.02;H, 4.46; N, 5.50. C$_{22}$H$_{22}$N$_2$O$_5$SCl$_2$ requires C, 53.12;H, 4.46; N, 5.63%); δH (DMSO-d$_6$, 400K) 7.63 (1H, brd, CONH), 7.51–7.38 (3H, m, OCH$_2$ArH), 7.16 (2H, d, J 8.7 Hz, CHCH$_2$ArH), 6.95 (2H, d, J 8.7 Hz, CHCH$_2$ArH), 5.26 (2H, s, OCH$_2$Ar), 4.83 (1H, dd, 3.9, 7.4, CH$_α$thiopro), 4.77 (1H, d, J 9.2 Hz, NCH$_A$H$_B$S), 4.53 (1H, dt, J 5.4, 8.3 Hz, CHαtyr), 4.37 (1H, d, J 9.2 Hz, NCH$_A$H$_B$S), 3.24 (1H, dd, J 7.3, 11.5 Hz, CHCH$_A$H$_B$S), 3.10 (1H, dd, J 5.4, 14.1 Hz, CHCH$_A$H$_B$Ar), 3.00 (1H, dd, J 3.9, 11.5 Hz, CHCH$_A$H$_B$S), 2.94 (1H, dd J 8.4, 14.1 Hz, CHCH$_A$H$_B$Ar) and 1.99 (3H, s, CH$_3$CO); m/z (ESI, 27V) 497 (M$^+$+1).

EXAMPLE 9
N-Acetyl-D-thioproline-(O-2,6-dichlorobenzyl)-3-nitro-L-tyrosine methyl ester A solution of Intermediate 4 (596 mg, 1.5 mmol) in DMF (5 ml) was added to a suspension of sodium hydride (60% in mineral oil, 66 mg, 1.65 mmol) in DMF (10 ml) at 0°. After 10 min a solution of 2,6-dichlorobenzyl bromide (432 mg, 1.8 mmol) in DMF (3 ml) was added and the mixture stirred at 0° for 2 h and at room temperature for 1 h. The reaction was quenched with a few drops of water and the DMF removed in vacuo. The residue was dissolved in ethyl acetate (100 ml), washed with water (2×30 ml) and brine (30 ml), dried (Na$_2$SO$_4$) and evaporated in vacuo. The residue was purified by column chromatography (SiO$_2$; methanol/DCM 5:95) to give the title compound as a yellow oil (600 mg, 72%); δH (DMSO-d$_6$, 300K) (2 rotameric species observed) 8.63 (d, J 8.0 Hz) and 8.37 (d, J 8.3 Hz) together (1H, CONH), 7.75–7.71 (1H, m, CHCH$_2$ArH), 7.58–7.45 (5H, m, ArH), 5.38 (2H, s, OCH$_2$Ar), 4.75–4.68 (m) and 4.56–4.48 (m) and 4.44 (d, J 8.6 Hz) and 4.20 (d, J 9.7 Hz) together (4H, 2×CH$_α$+NCH$_2$S), 3.66 (3H, s, CO$_2$CH$_3$), 3.29–2.73 (4H, m, CHCH$_2$Ar+CHCH$_2$S) and 2.04 (s) and 1.85 (s) together (3H, CH$_3$CO); m/z (ES, 15V) 556 (M$^+$+1).

EXAMPLE 10
N-Acetyl-D-thioproline-(O-2,6-dichlorobenzyl)-3-nitro-L-tyrosine

Lithium hydroxide (49 mg, 1.17 mmol) was added to a solution of the compound of Example 9 (590 mg, 1.06 mmol) in a mixture of THF (10 ml) and water (10 ml). The mixture was stirred at room temperature for 30 min then the THF was evaporated in vacuo. The aqueous residue was acidified (1M, hydrochloric acid) and extracted with ethyl acetate (2×75 ml). The combined extracts were dried (Na$_2$SO$_4$) and evaporated in vacuo. The residue was freeze dried from a mixture of methanol and water to give the title compound as a fluffy yellow solid (510 mg, 89%) (Found: C, 48.39; H, 3.91; N, 7.60. C$_{22}$H$_{21}$N$_3$O$_7$SCl$_2$ requires C, 48.72;H, 3.90; N, 7.75%); δH (DMSO-d$_6$, 400K) 7.85 (1H, br d, CONH), 7.67 (1H, d, J 2.2 Hz, ArH), 7.54–7.41 (5H, m, ArH), 5.44 (2H, s, OCH$_2$Ar), 4.82 (1H, dd, J 4.0, 7.3 Hz, CH$_α$thiopro), 4.76 (1H, d, J 9.1 Hz, NCH$_A$H$_B$S), 4.57 (1H, dt, J 5.2, 8.7 Hz, CH$_α$tyr), 4.37 (1H, d, J 9.2 Hz, NCH$_A$H$_B$S), 3.28–3.16 (2H, m, CHCH$_A$H$_B$Ar+CHCH$_A$CH$_B$S), 3.06–2.98 (2H, m, CHCH$_A$H$_B$Ar+CHCH$_A$H$_B$S) and 1.99 (3H, s, CH$_3$CO); m/z (ES, 30V) 542 (M$^+$+1).

EXAMPLE 11
N-Acetyl-D-thioproline-α-methyl-(O-2,6-dichlorobenzoyl)-L-tyrosine methyl ester A solution of Intermediate 6 (347 mg, 0.948 mmol) in DMF (5 ml) was added to a suspension of sodium hydride (60% in mineral oil, 40 mg, 0.995 mmol) in DMF (5 ml) at room temperature. After 10 min 2,6-dichlorobenzoyl chloride (150 μl, 1.04 mmol) was added and the mixture stirred for 1 h. The reaction was quenched with a few drops of water and the DMF was evaporated in vacuo. The residue was dissolved in ethyl acetate (10 ml), washed with water (2×30 ml) and brine (30 ml), dried (Na$_2$SO$_4$) and evaporated in vacuo. The residue was purified by column chromatography (SiO$_2$, methanol/DCM 5:95) to give the title compound as a yellow gum (423 mg, 83%); δH (DMSO-d$_6$, 400K) 7.63–7.46 (4H, m, CONH+COArH), 7.30 (2H, d, J 8.8 Hz, ArH), 7.21 (2H, d, J 8.7 Hz, ArH), 4.86 (1H, dd, J 3.89, 7.4 Hz, CHαthiopro), 4.78 (1H, d, J 9.1 Hz, NCH$_A$H$_B$S), 4.44 (1H, d, J 9.1 Hz, NCH$_A$H$_B$S), 3.66 (3H, s, CO$_2$CH$_3$), 3.38–3.14 (4H, m, CHCH$_2$S+CH$_2$Ar), 2.05 (3H, s, CH$_3$CO) and 1.40 (3H, s, CCH$_3$); m/z (ES, 15V) 539 (M$^+$+1).

EXAMPLE 12
N-Acetyl-D-thioproline-α-methyl-(O-2,6-dichlorobenzoyl)-L-tyrosine Lithium hydroxide (34 mg, 0.82 mmol) was added to a solution of the compound of Example 11 in a mixture of THF (7 ml) and water (7 ml). The mixture was stirred at room temperature for 7 h and the THF was evaporated in vacuo. The aqueous residue was acidified (1M, hydrochloric acid) and extracted with DCM (2×75 ml). The extracts were dried (Na$_2$SO$_4$) and evaporated in vacuo. Purification by column chromatography (SiO$_2$, methanol/acetic acid/DCM, 5:5:90) and freeze drying from a mixture of methanol and water gave the title compound as a fluffy white solid (275 mg, 64%). (Found: C, 51.81;H, 4.18; N, 5.13. C$_{23}$H$_{22}$N$_2$O$_6$SCl$_2$, (H$_2$O)$_{0.4}$ requires C, 51.87;H, 4.32; N, 5.26%); δH (DMSO-d$_6$, 400K) 7.63–7.54 (3H, m, COArH), 7.43 (1H, br s, CONH), 7.31 (2H, d, J 8.7 Hz, ArH), 7.19 (2H, d, J 8.7 Hz, ArH), 4.86 (1H, dd, J 3.9, 7.4 Hz, CHαthiopro), 4.79 (1H, d, J 9.2 Hz, NCH$_A$H$_B$S), 4.42 (1H, d, J 9.2 Hz, NCH$_A$H$_B$S), 3.38–3.26 (3H, m, CH$_A$H$_B$Ar+CHCH$_A$H$_B$S), 3.17 (1H, dd, J 3.9, 11.5 Hz, CHCH$_A$H$_B$S), 2.02 (3H, s, CH$_3$CO) and 1.45 (3H, s, CCH$_3$); m/z (ES, 15V) 525 (M$^+$+1).

EXAMPLE 13
N-Acetyl-D-thioproline-(O-2,4,6-trichlorobenzyl)-L-tyrosine methyl ester A solution of Intermediate 2 (528 mg, 1.5 mmol) in DMF (5 ml) was added to a suspension of sodium hydride (60% in mineral oil, 66 mg, 1.65 mmol) in DMF (5 ml) at 0°. After 10 min a solution of Intermediate 8 (453 mg, 1.65 mmol) in DMF (5 ml) was added and the mixture stirred at 0° for 2 h. The reaction was quenched with a few drops of water and the DMF was removed in vacuo. The residue was dissolved in ethyl acetate (150 ml), washed with water (2×50 ml) and brine (25 ml), dried ($Na_2SO_4$) and evaporated in vacuo. The residue was purified by column chromatography ($SiO_2$, ethyl acetate/hexane, 90/10) to give the title compound as a colouless viscous oil (619 mg, 76%); δH (DMSO-$d_6$, 300K) (2 rotameric species observed) 8.57 (d, J 8.2 Hz) and 8.31 (d, J 8.2 Hz) together (1H, CONH), 7.77 (2H, s, OCH$_2$ArH), 7.15 (2H, t, J 8.0 Hz, CHCH$_2$ArH), 6.97–6.93 (2H, m, CHCH$_2$ArH), 5.15 (2H, s, OCH$_2$Ar), 4.79–4.67 (m) and 4.50–4.43 (m) and 4.46 (d, J 8.7 Hz) and 4.22 (d, J 9.7 Hz) together (4H, 2×CH$_{\alpha+NCH2}$S), 3.63 (s) and 3.64 (s) together (3H, CO$_2$CH$_3$), 3.31–2.69 (4H, m, CHCH$_2$Ar+CHCH$_2$S) and 2.05 (s) and 1.83 (s) together (3H, CH$_3$CO); m/z (ES, 60V) 545 (M$^+$+1).

EXAMPLE 14
N-Acetyl-D-thioproline-(O-2,4,6-trichlorobenzyl)-L-tyrosine

Lithium hydroxide (52 mg, 1.23 mmol) was added to a solution of the compound of Example 13 (610 mg, 1.12 mmol) in a mixture of THF (11 ml) and water (11 ml). The mixture was stirred at room temperature for 30 min and the THF removed in vacuo. The aqueous residue was acidified (1 M hydrochloric acid) and extracted with DCM (2×50 ml). The combined extracts were dried (Na$_2$SO$_4$) and evaporated in vacuo. The residue was freeze dried from a mixture of methanol and water to give the title compound as a fluffy white solid (538 mg, 90%). (Found: C, 49.17;H, 3.99; N, 5.18. $C_{22}H_{21}N_2O_5SCl_3$. 0.25 ($H_2O$) requires C, 49.27; H, 4.04; N, 5.22%); δH (DMSO-$d_6$, 400K) 7.65 (1H, br d, CONH), 7.61 (2H, s, OCH$_2$ArH), 7.16 (2H, d, J 8.7 Hz, CHCH$_2$ArH), 6.95 (2H, d, J 8.7 Hz, CHCH$_2$ArH), 5.23 (2H, s, OCH$_2$Ar), 4.82 (1H, dd, J 3.9, 7.4 Hz, CH$_\alpha$thiopro), 4.77 (1H, d, J 9.2 Hz, NCH$_A$H$_B$S), 4.52 (1H, dt, J 5.4, 8.3 Hz, CH$_\alpha$tyr), 4.37 (1H, d, J 9.2 Hz, NCH$_A$H$_B$S), 3.24 (1H, dd, J 7.4, 11.5, Hz, CHCH$_A$H$_B$S), 3.10 (1H, dd, J 5.4, 14.2 Hz, CHCH$_A$H$_B$Ar), 3.00 (1H, dd, J 3.9, 11.5 Hz, CHCH$_A$H$_B$S), 2.93 (1H, dd, J 8.4, 14.2 Hz, CHCH$_A$H$_B$Ar) and 1.98 (3H, s, CH$_3$CO); m/z (ES, 60V) 531 (M$^+$+1).

EXAMPLE 15
N-Acetyl-D-thioproline-(O-2,6-difluorobenzyl)-L-tyrosine methyl ester Caesium carbonate (0.609 g, 1.87 mmol) was added in one portion to a solution of Intermediate 2 (0.60 g, 1.70 mmol) in DMF (15 ml). α-Bromo-2,6-difluorotoluene (0.387 g, 1.87 mmol) was then added and the reaction stirred for 16 h at room temperature. The reaction was partitioned between ethyl acetate (50 ml) and water (30 ml). The organic layer was separated and the aqueous layer was extracted with ethyl acetate (2×50 ml). The combined organic layers were washed with brine (50 ml), dried over MgSO$_4$ and the solvent removed under vacuum to give a white, waxy solid (1.0 g). Trituration with diisopropyl ether gave a white solid which was isolated by filtration, washed with diisopropyl ether and dried to give the title compound (0.69 g, 85%). δH (DMSO-$d_6$, 390K) 7.84 (1H, br d, CONH), 7.52–7.42 (1H, m, OCH$_2$ArH), 7.15–7.06 (4H, m, OCH$_2$ArH+CHCH$_2$ArH), 6.93 (2H, d, J 8.4 Hz, CHCH$_2$ArH), 5.13 (2H, s, OCH$_2$Ar), 4.82 (1H, dd, J 3.9, 7.2 Hz, CH$_\alpha$thiopro), 4.76 (1H, d, J 9.2 Hz, NCH$_A$H$_B$S), 4.56 (1H, dt, J 5.8, 8.2 Hz, CH$_\alpha$tyr), 4.38 (1H, d, J 9.3 Hz, NCH$_A$H$_B$S), 3.65 (3H, S, CO$_3$CH$_3$), 3.25 (1H, dd, J 7.4, 11.4 Hz, CHCH$_A$H$_B$S), 3.10–2.91 (3H, m, CHCH$_2$Ar+CHCH$_A$H$_B$S) and 1.99 (3H, s, CH$_3$CO); m/z (ES) 479 (M$^+$+1).

EXAMPLE 16
N-Acetyl-D-thioproline-(O-2,6-difluorobenzyl)-L-tyrosine

A solution of the compound of Example 15 (0.69 g, 1.44 mmol) in dioxane/methanol (1:1, 8 ml) and water (6 ml) was treated with lithium hydroxide monohydrate (72.6 mg, 1.73 mmol) in one portion. A further 1 ml of dioxane was added to give a clear solution. The reaction was stirred for 1.5 h at room temperature and then acidified to pH 4.5 with a few drops of glacial acetic acid to give a whiter precipitate. The bulk of solvent was removed in vacuo, water (5 ml) added and the solid isolated by filtration, washed well with water (20 ml), hexane (20 ml) and dried under vacuum to give the title compound as a white solid (0.56 g, 96%). δH (DMSO-$d_6$, 390K) 7.69 (1H, br d, CONH), 7.53–7.42 (1H, m, OCH$_2$ArH), 7.16–7.06 (4H, m, OCH$_2$ArH+CHCH$_2$ArH), 6.93 (2H, d, J 8.6 Hz, CHCH$_2$ArH), 5.12 (2H, s, OCH$_2$Ar), 4,82 (1H, dd, J 3.9, 7.3 Hz, CH$_\alpha$thiopro), 4.77 (1H, d, J 9.2 Hz, NCH$_A$H$_B$S), 4.50 (1H, dt, J 5.4, 8.3 Hz, CH$_\alpha$tyr), 4.37 (1H, d, J 9.0 Hz, NCH$_A$H$_B$S), 3.24 (1H, dd, J 7.4, 11.5 Hz, CHCH$_A$H$_B$S), 3.08 (1H, dd, J 5.4, 14.1 Hz, CHCH$_A$H$_B$Ar), 2.99 (1H, dd, J 3.9, 11.5 Hz, CHCH$_A$H$_B$S), 2.92 (1H, dd, J 8.5, 14.2 Hz, CHCH$_A$H$_B$Ar) and 1.98 (3H, s, CH$_3$CO); m/z (ES) 4.65 (M$^+$+1).

The following compounds of Examples 17–44 were prepared by a similar method to the compound of Example 16. Each starting ester was prepared by one of the procedures described for the preparation of the esters of Examples 1, 3, 5, 7, 9, 11, 13 or 15, using the appropriate thioproline starting material prepared according to the procedures of Intermedites 1–6.

EXAMPLE 17
N-Acetyl-L-thioproline-(O-methyl)-L-tyrosine

δH (DMSO-d$^6$, 380K) 7.68 (1H, br s, CONH), 7.13 (2H, d, J 8.6 Hz, ArH), 6.82 (2H, d, J 8.7 Hz, ArH), 7.13 (2H, d, J 8.6 Hz, ArH), 6.82 (2H, d, J 8.7 Hz, ArH), 4.79 (1H, br m, CHαthiopro), 4.74 (1H, d, J 9.2 Hz, NCH$_A$H$_B$S), 4.50 (1H, dt, J 8.2, 5.4 Hz, CHαtyr), 4.33 (1H, d, J 9.3 Hz, NCH$_A$H$_B$S), 3.73 (3H, s, OMe), 3.26 (1H, m, CHCH$_A$H$_B$S), 3.10–3.03 (2H, m, CHCH$_A$H$_B$S+CHCH$_A$H$_B$Ar), 2.92 (1H, dd, J 8.4, 1.41 Hz, CHCH$_A$H$_B$Ar) and 1.94 (3H, s, COCH$_3$) (acid proton not observed at 380K); m/z (ESI, 27V) 353 (M$^+$+1).

EXAMPLE 18
N-Acetyl-L-thioproline-(O-benzyl)-L-tyrosine m.p. 177–178°. δH (DMSO-d$^6$, 400K) 7.6 (1H, br d, CONH), 7.43–7.29 (5H, m, Ph), 7.13 (2H, d, J 8.6 Hz, ArH), 6.90 (2H, d, J 8.6 Hz, ArH0, 5.07 (2H, s, OCH$_2$Ph), 4.81 (1H, dd, J 7.6, 3.9 Hz, CHαthiopro), 4.73 (1H, d, J 9.2 Hz, NCH$_A$H$_B$S), 4.52 (1H, dt, J 8.2, 5.5 Hz, CHαtyr), 3.26 (1H, dd, J 11.4, 7.4 Hz, CHCH$_A$H$_B$S), 3.09 (1H, dd, J 11.5, 3.7 Hz, CHCH$_A$H$_B$S), 3.07 (1H, dd, J 14.2, 5.4 Hz, CHCH$_A$H$_B$Ar), 2.92 (1H, dd, J 14.2, 8.2 Hz, CHCH$_A$H$_B$Ar) and 1.95 (3H, s, COCH$_3$) (acid proton not observed at 400K); m/z (ESI, 40V) 429 (M$^+$+1).

EXAMPLE 19
N-Acetyl-L-thioproline-(O-phenylethyl)-L-tyrosine

δH (DMSO-d$^6$, 400K) 7.55 (1H, brs, CONH), 7.29–7.15 (5H, m, Ph), 7.11 (2H, d, J 8.7 Hz, ArH), 6.81 (2H, d, J 8.7 Hz, ArH), 4.81 (1H, dd, J 7.3, 3.8 Hz, CHαthiopro), 4.74 1H, d, J 9.3 Hz, NCH$_A$H$_B$S), 4.47 (1H, m, CHαtyr), 4.31 (1H, d, J 9.3 Hz, NCH$_A$H$_B$S), 4.20 (2H, t, J 6.7 Hz, OCH$_2$CH$_2$Ph), 3.26 (1H, dd, J 11.4, 7.4 Hz, CHCH$_A$H$_B$S), 3.10 (1H, dd, J 11.5, 3.7 Hz, CHCH$_A$H$_B$S), 3.05 (1H, signal obscured, CHCH$_A$H$_B$Ar), 3.02 (2H, t, J 6.7 Hz, OCH$_2$CH$_2$Ph), 2.91 (1H, dd, J 14.1, 7.9 Hz, CHCH$_A$H$_B$Ar) and 1.95 (3H, s, COCH$_3$) (acid proton not observed at 400K); m/z (ESI, 15V), 443 (M$^+$+1).

EXAMPLE 20
N-Acetyl-L-thioproline-(O-benzoyl)-L-tyrosine m.p. 187–188°. δH (DMSO-d$^6$, 400K) 8.11 (2H, d, J 8.0 Hz, PhH), 7.73–7.68 (2H, m, CONH+PhH), 7.58 (2H, t, J 7.6 Hz, PhH), 7.31 (2H, d, J 8.5 Hz, ArH), 7.18 (2H, d, J 8.5 Hz, ArH), 4.85 (1H, m, CHαthiopro), 4.75 (1H, d, J 9.3 Hz, NCH$_{AB}$S), 4.60 (1H, dt, J 5.4, 8.2 Hz, CHαtyr), 4.36 (1H, d, J 9.2 Hz, NCH$_A$H$_B$S), 3.28 (1H, dd, J 11.4, 7.4 Hz, CHCH$_A$H$_B$S), 3.18 (1H, dd, J 14.1, 5.5 Hz, CHCH$_A$H$_B$Ar), 3.11 (1H, dd, J 11.5, 3.8 Hz, CHCH$_A$H$_B$S), 3.03 (1H, dd, J 14.1, 8.4 Hz, CHCH$_A$H$_B$Ar) and 1.97 (3H, s, COCH$_3$) (acid proton not observed at 400K); m/z (ESI, 27V) 443 (M$^+$+1).

EXAMPLE 21
N-Acetyl-D-thioproline-(O-benzoyl)-L-tyrosine

δH (DMSO-d$^6$, 400K) 8.11 (2H, d, J 7.8 Hz, PhH), 7.8–7.68 (2H, m, CONH+PhH), 7.58 (2H, t, J 7.5 Hz, PhH), 7.30 (2H, d, J 8.5 Hz, ArH), 7.18 (2H, d, J 8.5 Hz, ArH), 4.83 (1H, dd, J 7.2, 3.8 Hz, CHαthiopro), 4.77 (1H, d, J 9.2 Hz, NCH$_A$H$_B$S), 4.57 (1H, dt, J 8.3, 5.5 Hz, CHαtyr), 4.38 (1H, d, J 9.2 Hz, NCH$_A$H$_B$S), 3.26 (1H, dd, J 11.5, 7.3 Hz, CHCH$_A$H$_B$S), 3.18 (1H, dd, J 14.1, 5.3 Hz, CHCH$_A$H$_B$Ar), 3.06–2.99 (2H, m, CHCH$_A$H$_B$S+CHCH$_A$H$_B$Ar) and 2.00 (3H, s, COCH$_3$) (acid proton not observed at 400K); m/z (ESI, 15V) 443 (M$^+$+1).

EXAMPLE 22
N-Acetyl-D-thioproline-(N-methyl)(O-benzyl)-L-tyrosine

δH (DMSO-d$^6$, 400K) 7.42–7.29 (5H, m, Ph), 7.15 (2H, d, J 8.3 Hz, ArH), 6.90 (2H, d, J 8.3Hx, ArH), 5.1 (1H, br m, CHαthiopro),5.06 (2H, S, OCH$_2$Ph), 4.9 (1H, br m, CHαtyr), 4.75 (1H, d, J 9.0 Hz, NCH$_A$H$_B$S), 4.38 (1H, d, J 8.9 Hz, NCH$_A$H$_B$S), 3.35–3.20 and 3.0–2.9 (4H, m, CHCH$_2$S+CHCH$_2$Ar), 2.90 (3H, br s, NMe) and 1.9 (3H, v br s, COCH$_3$) (acid proton not observed at 400K); m/z (ESI, 15V) 443 (M$^+$+1).

EXAMPLE 23
N-Acetyl-D-thioproline-(O-trifluoromethylsulphonyl)-L-tyrosine

δH (DMSO-d$^6$, 400K) 7.8 (1H, br d, CONH), 7.40 (2H, d, J 8.8 Hz, ArH), 7.30 (2H, d, J 8.8 Hz, ArH), 4.79 (1H, dd, J 7.3, 3.8 Hz, CHαthiopro), 4.75 (1H, d, J 9.2 Hz, NCH$_A$H$_B$S), 4.57 (1H, dt, J 8.7, 4.9 Hz, CHαtyr), 4.36 (1H, d, J 9.2 Hz, NCH$_A$H$_B$S), 3.26–3.18 (2H, m, CHCH$_A$H$_B$S+CHCH$_A$H$_B$Ar),3.04 (1H, dd, J 14.2, 8.8 Hz, CHCH$_A$H$_B$Ar), 2.97 (1H, dd, J 11.6, 3.9 Hz, CHCH$_A$H$_B$S) and 1.97 (3H, s, COCH$_3$) (acid proton not observed at 400K); m/z (ESI, 15V) 471 (M$^+$+1).

EXAMPLE 24
N-Acetyl-D-thioproline-(O-tert.butyl)-L-tyrosine

δH (DMSO-d$^6$, 300K) (2 rotameric species observed) 9.86 (1H, br s, CO$_2$H), 7.26–7.21 (m) and 7.05–7.02 (m) together (3H, NH and ArH), 6.86 (2H, d, J 8.32 Hz, ArH), 4.95–4.31 (4H, m, CHα-tyr, CHα-thiopro and NCH$_2$S), 3.22–2.88 (4H, m, CH$_2$Ar and CHCH$_2$S), 2.13 (s) and 2.10 (s) together (3H, CH$_3$CO) and 1.27 (9H, s, C(CH$_3$)$_3$); m/z (ESI, 60V) 395 (M$^+$+1).

EXAMPLE 25
N-Acetyl-L-thioproline-(O-2,6-dichlorobenzyl)-L-tyrosine

δH (DMSO-d$^6$, 390K) 7.65 (1H, br s, NH), 7.51–7.39 (3H, m, Cl$_2$-Ar-H), 7.17 (2H, ABd, J 8.7 Hz, Ar-H), 6.95 (2H, ABd, J 8.7 Hz, Ar-H), 5.25 (2H, s, CH$_2$OPh), 4.81 (1H, m, CHα-thiopro), 4.74 (1H, d, J 9.2 Hz, NCH H$_B$S), 4.54 (1H, ddd, J 13.6, 8.3, 5.4 Hz, CHα-tyr), 4.34 (1H, d, J 9.2 Hz, NCH$_A$H$_B$S), 3.28 (1H, dd, J 11.4, 7.4 Hz, CHCH$_A$H$_B$Ar) 3.09 (2H, m, CHCH$_2$S), 2.94 (1H, dd, J 14.1, 8.3 Hz, CHCH$_A$H$_B$Ar) and 1.96 (3H, s, MeCO). m/z (ESI, 60V) 497, 499 (M$^+$+1).

EXAMPLE 26
N-Acetyl-D-thioproline-(O-3,5-dichlorobenzyl)-L-tyrosine

δH (DMSO-d$^6$, 390K) 7.71 (1H, br d, NH), 7.45 (3H, s, Cl$_2$Ar-H), 7.15 (2H, m, Ar-H), 6.94 (2H, m, Ar-H), 5.10 (2H, s, CH$_2$OAr), 4.81 (1H, m, CHα-thiopro), 4.76 (1H, d, J 9.2 Hz, NCH$_A$H$_B$S), 4.49 (1H, m, CHαtyr), 4.36 (1H, d, J 9.2 Hz, NCH$_A$H$_B$S), 3.26–2.91 (4H, m, CHCH$_2$S+CHCH$_2$Ar), 1.97 (3H, s, MecO). m/z (ESI, 60V), 497 (M$^+$+1).

EXAMPLE 27
N-Acetyl-D-thioproline-(O-2-trifluoromethylbenzyl)-L-tyrosine

δH (DMSO-d$^6$, 390K) 7.76–7.65 (4H, m, CF$_3$-ArH+NH), 7.57 (1H, t, J 8.0 Hz, CF$_3$-Ar-H), 7.16 (2H, m, Ar-H), 6.92 (2H, m, Ar-H), 5.23 (2H, s, CH$_2$OAr), 4.81 (1H, m, CHα-thiopro), 4.76 (1H, d, J 9.2 Hz, NCH$_A$H$_B$S), 4.50 (1H, m, CHαtyr), 4.36 (1H, d, J 9.2 Hz, NCH$_A$H$_B$S), 3.26–2.88 (4H, m, CHCH$_2$Ar+CHCH$_2$S), 1.97 (3H, s, MeCO). m/z (ESI, 80V), 497 (M$^+$+1).

EXAMPLE 28
N-Acetyl-D-thioproline-(O-2-dichlorobenzyl)-3-methoxytyrosine

δH (DMSO-d$^6$) as a diastereomeric mixture 7.58 (1H, br s, NH), 7.51–7.40 (3H, m, Cl$_2$-Ar-H), 7.06 (1H, dd, J 8.3, 1.5 Hz, MeOAr-H), 6.62 (1H, d, J 2.4 Hz, MeOAr-H), 6.57 (1H, m, MeOAr-H), 5.27 (2H, s, CH$_2$OAr), 4.76 (d, J 9.2 Hz) and 4.75 (d, J 9.3 Hz) together (1H, NCH$_A$H$_B$S), 4.75 (1H, m, CHα-thiopro), 4.54 (1H, m, CHαtyr), 4.35 (d, J 9.3 Hz) and 4.29 (d, J 9.2 Hz) together (1H, NCH$_A$H$_B$S), 3.80 (3H, s, OMe), 3.29–2.80 (4H, m, CHCH$_2$Ar+CHCH$_2$S), 1.97 (s) and 1.95 (s) together (3H, MeCO). m/z (ESI, 60V), 527, 529 (M$^+$+1).

EXAMPLE 29
N-Acetyl-D-thioproline-(O-4'-acetamidophenyl)-L-tyrosine

δH (DMSO-d$^6$ 400K), 7.7 (1H, br d, CONH), 7.53 (2H, d, J 9.0 Hz, ArH), 7.20 (2H, d, J 8.7 Hz, ArH), 6.92 (2H, d, J 9.2 Hz, ArH), 6.89 (2H, d, J 8.9 Hz, ArH), 4.82 (1H, dd, J 7.5, 3.9 Hz, CHαthiopro), 4.77 (1H, dt, J 9.2 Hz, NCH$_A$H$_B$S), 4.54 (1H, dt, J 8.3, 5.4 Hz, CHαtyr), 4.38 (1H, d, J 9.3 Hz, NCH$_A$H$_B$S), 3.25 (1H, DD, J 11.5, 7.4 Hz, CHCH$_A$H$_B$S), 3.08 (1H, dd, J 14.2, 5.4 Hz, CHCH$_A$H$_B$Ar), 2.99 (1H, dd, J 11.6, 4.0 Hz, CHCH$_A$H$_B$S), 2.95 (1H, dd, J 14.2, 8.7 Hz, CHCH$_A$H$_B$Ar), 2.03 (3H, s, COCH$_3$) and 1.99 (3H, s, COCH$_3$) (acid proton and other amide proton not observed at 400K); m/z (ESI, 15V) 472 (M$^+$+1).

EXAMPLE 30
N-Acetyl-D-thioproline-(O-phenylaminocarbonyl)-L-tyrosine

δH (DMSO-d$^6$, 300K), (2 rotameric species observed) 12.8 (1H, br s, CO$_2$H), 10.16 (1H, s, CONHPh), 8.49 (d, J 8.3 Hz) and 8.23 (d, J 8.3 Hz) together (1H, CONH), 7.50 (2H, d, J 8.1 Hz, ArH), 7.31 (2H, t, J 7.9 Hz, ArH), 7.24 (2H, d, J 8.5 Hz, ArH), 7.12 (d, J 8.3 Hz) and 7.11 (d, J 8.4 Hz) together (2H, ArH), 7.04 (1H, t, J 7.3 Hz, ArH), 4.80–4.67 (3H, m, CHαthiopro+NCH$_A$H$_B$S), 4.55–4.40 (1H, m, CHαtyr), 4.45 (d, J 8.8 Hz) and 4.22 (d, J 9.8 Hz) together (1H, NCH$_A$H$_B$S), 3.4–2.7 (4H, m, CHCH$_A$H$_B$Ar+CHCH$_2$S), 2.05 (s) and 1,83 (s) together (3H, COCH$_3$) m/z (ESI, 15V) 458 (M$^+$+1).

EXAMPLE 31
N-Acetyl-D-thioproline-(O-2'-nitrophenyl)-L-tyrosine

δH (DMSO-d$^6$ 400K), 7.97 (1H, dd, J 8.1, 1.6 Hz, (NO$_2$)ArH), 7.7 (1H, v br d, CONH), 7.64 (1H, ddd, J 8.4, 7.5, 1.7 Hz, (NO$_2$)ArH), 7.33 (1H, ddd, J 8.1, 7.5, 1.2 Hz, (NO$_2$)ArH), 7.27 (2H, d, J 8.7 Hz, ArH), 7.11 (1H, dd, J 8.4, 1.2 Hz, (NO$_2$)ArH), 6.97 (2H, d, J 8.7 Hz, ArH), 4.82 (1H, dd, J 7.4, 4.0 Hz, CHαthiopro), 4.77 (1H, d, J 9.2 Hz, NCH$_A$H$_B$S), 4.56 (1H, dt, J 8.5, 5.4 Hz, CHαtyr), 4.38 (1H, d, J 9.2 Hz, NCH$_A$H$_B$S), 3.25 (1H, dd, J 11.5, 7.4 Hz, CHCH$_A$H$_B$S), 3.16 (1H, DD, J 14.1, 5.3 Hz, CHCH$_A$H$_B$Ar), 3.01 (1H, dd, J 11.5, 3.9 Hz, CHCH$_A$H$_B$S), 2.98 (1H, signal obscured, CHCH$_A$H$_B$Ar) and 1.99 (3H, s, COCH$_3$) (acid proton not observed at 400K); m/z (ESI, 27V) 460 (M$^+$+1).

EXAMPLE 32A

N-Acetyl-D-thioproline-S,S-dioxide(O-benzyl)-L-tyrosine

δH (DMSO-d$^6$ 400K), 7.793(1H, brd, CONH), 7.44–7.30 (5H, m, Ph), 7.13 (2H, d, J 8.7 Hz, ArH), 6.93 (2H, d, J 8.7 Hz, ArH), 5.19 (1H, dd, J 8.9, 4.9 Hz, CHαthiopro), 5.08 (2H, s, OCH$_2$Ph), 4.96 (1H, dt, J 11.9 Hz, NCH$_A$H$_B$S), 4.51 (1H, dt, J 8.2, 5.5 Hz, CHαtyr), 4.29 (1H, d, J 11.8 Hz, NCH$_A$H$_B$S), 3.56 (1H, dd, J 13.6, 8.9HZ, CHCH$_A$H$_B$S), 3.19 (1H, dd, J 13.6, 5.0 Hz, CHCH$_A$H$_B$S), 3.09 (1H, dd, J 14.2, 5.5 Hz, CHCH$_A$H$_B$Ar), 2.91 (1H, dd, J 14.2, 8.4 Hz, CHCH$_A$H$_B$Ar) and 2.03 (3H, s, COCH$_3$) (acid proton not observed at 400K); m/z (ESI, 27V) 461 (M$^+$+1).

EXAMPLE 32B
N-Acetyl-L-thioproline-(O-2,6-dichlorobenzoyl)-D-tyrosine

δH (DMSO-d$^6$ 400K), 7.75(1H, br d, CONH), 7.63–7.54 (3H, m, ClArH), 7.35 (2H, d, J 8.7 Hz, ArH), 7.20 (2H, d, J 8.6 Hz, ArH), 4.83 (1H, dd, J 7.4, 3.9 Hz, CHαthiopro), 4.77 (1H, d, J 9.2 Hz, NCH$_A$H$_B$S), 4.57 (1H, m, CHαtyr), 4.38 (1H, d, J 9.3 Hz, NCH$_A$H$_B$S), 3.25 (1H, dd, J 11.5, 7.4 Hz, CHCH$_A$H$_B$S), 3.20 (1H, dd, J 14.3, 5.4 Hz, CHCH$_A$H$_B$Ar), 23.08–3.00 (2H, m, CHCH$_A$H$_B$S+ CHCH$_A$H$_B$Ar) and 1.99 (3H, s, COCH$_3$) (acid proton not observed at 400K); m/z (ESI, 15V) 511 (M$^+$+1).

EXAMPLE 33
N-Acetyl-D-thioproline-S-oxide-(O-2,6-dichlorobenzyl)-L-tyrosine

δH (DMSO-d$^6$ 390K), 8.04 (1H, br s, NH), 7.51 (1H, d, J 9.3 Hz, Cl$_2$-Ar-H), 7.50 (1H, d, J 6.5, Cl$_2$-Ar-H), 7.42 (1H, dd, J 9.3, 6.5 Hz, Cl$_2$-Ar-H), 7.16 (1H, d, J 8.6 Hz, Ar-H), 6.97 (2H, d, J 8.6 Hz, Ar-H), 5.26 (2H, s, CH$_2$OAr), 5.16 (1H, m, CHαthiopro), 4.99 (1H, d, J 12.9 Hz, NCH$_A$H$_B$SO), 4.51 (1H, m, CHαtyr), 4.14 (1H, d, J 12.9 Hz, NCH$_A$H$_B$SO), 3.21–2.85 (4H, m, CHCH$_2$SO+CHCH$_2$Ar), 2.05 (3H, s, MeCO); m/z (ESI, 60V) 513 (M$^+$+1).

EXAMPLE 34
N-Acetyl-D-thioproline-S,S-dioxide-(O-2,6-dichlorobenzyl)-L-tyrosine δH (DMSO-d$^6$ 390K), 8.04 (1H, b s, NH), 7.51 (1H, d, J 9.3 Hz, Cl$_2$-Ar-H), 7.50 (1H, d, J 6.5, Cl$_2$-Ar-H), 7.42 (1H, dd, J 9.3, 6.5 Hz, Cl$_2$-Ar-H), 7.16 (2H, ABd, J 8.6 Hz, Ar-H), 6.96 (2H, ABd, J 8.6 Hz, Ar-H), 5.26 (2H, s, CH$_2$OAr), 5.19 (1H, dd, J 9.2, 5.0 Hz, CHαthiopro), 4.98 (1H, d, J 11.9 Hz, NCH$_A$H$_B$SO$_2$), 4.51 (1H, m, CHαtyr), 4.31 (1H, d, J 11.9 Hz, NCH$_A$H$_B$SO$_2$), 3.20–2.93 (4H, m, CHCH$_2$SO$_2$+ CHCH$_2$Ar), 2.05 (3H, s, MeCO); m/z (ESI, 60V) 529 (M$^+$+1).

EXAMPLE 35
N-Acetyl-D-thioproline-O[1-(2-methylnaphthyl)methyl]-L-tyrosine

δH (DMSO-d$^6$ 390K), 8.09 (1H, d, J 8.4 Hz, NapH), 7.88 (1H, d, J 7.9 Hz, Nap-H), 7.83 (1H, d, J 8.4 Hz, Nap-H), 7.67 (1H, br s, NH), 7.54–7.42 (3H, m, NapH), 7.17 (2H, ABd, J 8.6 Hz, Ar-H), 6.98 (2H, ABd, J 8.6 Hz, Ar-H), 5.49 (2H, s, CH$_2$OAr), 4.83 (1H, dd, J 7.2, 3.9 Hz, CHαthiopro), 4.78 NCH$_A$H$_B$S), 4.46 (1H, m, CHαtyr), 4.38 (1H, d, J 9.2 Hz, NCH$_A$H$_B$S), 3.25–2.90 (4H, m, CHCH$_2$S+CHCH$_2$Ar) and 1.98 (3H, s, MeCO); m/z (ESI, 60V) 493 (M$^+$+1).

EXAMPLE 36
N-Acetyl-D-thioproline-(O-x-methyl benzyl)-L-tyrosine δH (DMSO-d$^6$ 390K), 7.64 (1H, br d, NH), 7.40–7.20 (5H, m, Ph), 7.05 (2H, d, J 8.5 Hz, Ar-H), 6.81 (2H, m, J 8.5, Ar-H), 5.39 (1H, q, J 6.4 Hz, CHMe), 4.76 (1H, m, CHαthiopro), 4.75 (1H, d, J 9.1 Hz, NCH$_A$H$_B$S), 4.44 (1H, m, CHαtyr), 4.33 (1H, d, J 9.1 Hz, NCH$_A$H$_B$S), 3.22–2.82 (4H, m, CHCH$_2$SO+CHCH$_2$Ar), 1.95 (3H, s, MeCO) and 1.55 (3H, d, J 6.4 Hz, CHMe; m/z (ESI, 60V) 443 (M$^+$+1).

EXAMPLE 37
N-Acetyl-D-thioproline-(O-2,4,6-trichlorobenzoyl)-L-tyrosine

δH (DMSO-d$^6$ 390K), 7.80 (1H, br d, NH), 7.77 (2H, S Cl$_3$Ar-H), 7.35 (2H, ABd, J 8.6 Hz, Ar-H), 7.20 (2H, ABd, J 8.6 Hz, Ar-H), 4.81 (1H, m, CHαthiopro), 4.76 (1H, d, J 19.2 Hz, NCH$_A$H$_B$S), 4.57 (1H, m, CHαtyr), 4.38 (1H, d, J 9.2 Hz, NCH$_A$H$_B$S), 3.35–2.95 (4H, m, CHCH$_2$S+ CHCH$_2$Ar) and 1.99 (3H, s, MeCO); m/z (ESI, 60V) 544 (M$^+$+1).

EXAMPLE 38
N-Acetyl-D-thioproline-(O-phenylsulphonyl)-L-tyrosine

δH (DMSO-d$^6$ 400K), 7.88–7.62 (6H, m, Ph+CONH), 7.22 (2H, d, J 8.7 Hz, ArH), 6.97 (2H, d, J 8.7 Hz, ArH), 4.80 (1H, dd, J 7.4, 3.9 Hz, CHαthiopro), 4.76 (1H, d, J 9.1 Hz, NCH$_A$H$_B$S), 4.52 (1H, dt, J 8.6, 5.4 Hz, CHαtyr), 4.36 (1H, d, J 9.6 Hz, NCH$_A$H$_B$S), 3.23 (1H, dd, J 11.5, 7.4 Hz, CHCH$_A$H$_B$S), 3.13 (1H, dd, J 14.2, 5.4 Hz, CHCH$_A$H$_B$Ar), 3.00–2.93 (2H, m, CHCH$_A$H$_B$S+CHCH$_A$H$_B$Ar) and 1.98 (3H, s, COCH$_3$) (acid proton not observed at 400K); m/z (ESI, 15V) 479 (M$^+$+1).

EXAMPLE 39
N-Acetyl-D-thioproline-(O-benzyl)-3,5-dibromo-L-tyrosine δH (DMSO-d$^6$ 400K), 7.85 (1H br d, CONH), 7.57–7.36 (7H, m, ArH), 4.83 (1H, dd, J 7.4, 3.9 Hz, CHαthiopro), 4.77 (1H, d, J 9.1 Hz, NCH$_A$H$_B$S), 4.55 (1H, m, CHαtyr), 4.39 (1H, d, J 9.2 Hz, NCH$_A$H$_B$S), 3.28 (1H, dd, J 11.6, 7.4 Hz, CHCH$_A$H$_B$S), 3.15 (1H, dd, J 14.2, 5.3 Hz, CHCH$_A$H$_B$Ar), 3.02 (1H, dd, J 11.6, 3.8 Hz, CHCH$_A$H$_B$S), 2.97 (1H, dd, J 14.2, 88 Hz, CHCH$_A$H$_B$Ar) and 2.01 (3H, s, COCH$_3$) (acid proton not observed at 400K); m/z (ESI, 15V) 585 (M$^+$+1).

EXAMPLE 40
N-Acetyl-D-thioproline-(O-benzylaminocarbonyl)-L-tyrosine

δH (DMSO-d$^6$ 400K), 7.65 (1H, br, CONH), 7.56 (1H, br, CONH), 7.35–7.25 (5H, m, Ph), 7.20 (2H, d, J 8.5 Hz, ArH), 7.00 (2H, d, J 8.5 Hz, ArH), 4.82 (1H, dd, J 7.4, 4.0 Hz, CHαthiopro),4.66 (1H, d, J 9.2 Hz, NCH$_A$H$_B$S), 4.48 (1H, m, CHαtyr), 4.37 (1H, d, J 9.3 Hz, NCH$_A$H$_B$S), 4.32 (2H, d, J 6.1 Hz, NCH$_2$Ph), 3.24 (1H, dd, J 11.5, 7.4 Hz, CHCH$_A$H$_B$S), 3.13 (1H, dd, J 14.1, 5.3 Hz, CHCH$_A$H$_B$Ar), 3.03 (1H, dd, J 11.5, 3.9 Hz, CHCH$_A$H$_B$S), 2.98 (1H, dd, J 14.1, 7.9 Hz, CHCH$_A$H$_B$Ar) and 1.98 (3H, s, COCH$_3$) (acid proton not observed at 400K); m/z (ESI, 15V) 472 (M$^+$+1).

EXAMPLE 41
N-Acetyl-D-thioproline-(O-2',acetamidophenyl)-L-tyrosine

δH (DMSO-d$^6$ 400K), 8.76 (1H, br s, PhNHCO), 7.96–7.92 (1H, m, (CONH)ArH), 7.68 (1H, br d, CONH), 7.22 (2H, d, J 8.7 Hz, ArH), 7.10–7.03 (2H, m, (CONH) ArH), 6.91 (2H, d, J 8.7 Hz, ArH), 6.88–6.84 (1H, m, (CONH) ArH), 4.83 (1H, dd, J 7.3, 3.9 Hz, CHαthiopro), 4.77 (1H, d, J 9.2 Hz, NCH$_A$H$_B$S), 4.54 (1H, dt, J 8.4, 5.3 Hz, CHαtyr), 4.38 (1H, d, J 9.2 Hz, NCH$_A$H$_B$S), 3.26 (1H, dd, J 11.5, 7.4 Hz, CHCH$_A$H$_B$S), 3.14 (1H, dd, J 14.1, 5.4 Hz, CHCH$_A$H$_B$Ar), 3.02 (1H, dd, J 11.6, 3.9 Hz, CHCH$_A$H$_B$S), 2.96 (1H, dd, J 14.1, 8.5 Hz, CHCH$_A$H$_B$Ar), 2.03 (3H, s, COCH$_3$) and 1.99 (3H, s, COCH$_3$) (acid proton not observed at 400K); m/z (ESI, 30V) 472 (M$^+$+1).

EXAMPLE 42
N-Acetyl-D-thioproline-(O-2,6-dichlorobenzyl)-3-chloro-L-tyrosine δH (DMSO-d$^6$ 400K), 7.75 (1H, br d, CONH), 7.52–7.40 (3H, m, Cl$_2$ArH), 7.27–7.14 (3H, m, ClArH), 5.34 (2H, s, OCH$_2$Ar), 4.83 ((1H, dd, J 7.3, 3.9 Hz, CHαthiopro), 4.77 (1H, d, J 9.2 Hz, NCH$_A$H$_B$S), 4.53 (1H, dt, J 8.5, 5.2 Hz, CHαtyr), 4.38 (1H, d, J 9.2 Hz, NCH$_A$H$_B$S), 3.26 (1H, dd, J 11.4, 7.3 Hz, CHCH$_A$H$_B$S), 3.11 (1H, dd, J 14.2, 5.4 Hz, CHCH$_A$H$_B$Ar), 3.01 (1H, dd, J 11.5, 3.9 Hz, CHCH$_A$H$_B$S), 2.94 (1H, dd, J 14.1, 8.5 Hz, CHCH$_A$H$_B$Ar) and 2.00 (3H, s, COCH$_3$) (acid proton not observed at 400K); m/z (ESI, 30V) 531 (M$^+$+1).

EXAMPLE 43
N-Acetyl-D-thioproline-(N-methyl)(O-benzyl)-L-tyrosine

δH (DMSO-d$^6$ 400K) 7.44–7.29 (5H, m, Ph), 7.15 (2H, d, J 8.7 Hz, ArH), 6.92 (2H, d, J 8.7 Hz, AH), 5.16 (1H, m, CHαthiopro), 5.08 (2H, s, OCH$_2$Ph), 4.96 (1H, dd, J 9.9, 5.3 Hz, CHαtyr), 4.77 (1H, d, J 9.2 Hz, NCH$_A$H$_B$S), 4.37 (1H, d, J 9.2 Hz, NCH$_A$H$_B$S), 3.3 (1H, v br m, CHCH$_A$H$_B$S), 3.21 (1H, dd, J 14.6, 5.3 Hz, CHCH$_A$H$_B$Ar), 3.01 (1H, dd, J 14.6, 9.9 Hz, CHCH$_A$H$_B$Ar), 2.8 (1H, v br m, CHCH$_A$H$_B$S ), 2.93 (3H, s, NMe) and 1.84 (3H, br s, COCH$_3$) (acid proton not observed at 400K); m/z (ESI, 60V) 443 (M$^+$+1).

EXAMPLE 44
N-Acetyl-L-thioproline-(O-2,6-dichlorobenzoyl)-α-methyl-L-tyrosine δH (DMSO-d$^6$ 390K), 7.64–7.55 (3H, m, ClArH), 7.48 (1H, br s, CONH), 7.28 (2H, d, J 8.6 Hz, ArH), 7.19 (2H, d, J 8.6 Hz, ArH), 4.87 (1H, dd, J 7.2, 3.6 Hz, CHαthiopro), 4.76 (1H, d, J 9.2 Hz, NCH$_A$H$_B$S), 4.38 (1H, d, J 9.2 Hz, NCH$_A$H$_B$S), 3.30 (2H, s, CH$_2$Ar), 3.30 (1H, signal obscured CHCH$_A$H$_B$S), 3.17 (1H, dd, J 11.5, 3.6 Hz, CHCH$_A$H$_B$S), 2.02 (3H, s, COCH$_3$) and 1.48 (CMe) (acid proton not observed at 400K); m/z (ESI, 60V) 525 (M$^+$+1).

EXAMPLE 45
N-(4'-Acetamidophenylacetyl)-D-thioproline-(O-benzyl)-L-tyrosine methyl ester EDC. HCl (158 mg, 0.82 mmol) was added to a solution of Intermediate 10 (300 mg, 0.75 mmol), 4-acetamidophenylacetic acid (159 mg, 0.82 mmol), and HOBT (122 mg, 0.90 mmol) in DMF (5 ml) and the reaction stirred for 4 h at room temperature. The DMF was removed in vacuo and the residue partitioned between ethyl acetate (20 ml) and 5% aqueous Na$_2$CO$_3$ (20 ml). The aqueous phase was separated and extracted with ethyl acetate (2×10 ml). The combined organic phases were washed with brine (10 ml), and dried (Na$_2$SO$_4$) to give an oil which was purified by chromatography (SiO$_2$, ethyl acetate) to give the title compound as a colourless foam (320 mg, 74%). δH (DMSO-d$^6$) (2 rotameric species observed). 9.87 (1H, s, ArNHCO), 8.66 (br d, J 7.9 Hz) and 8.31 (br d, J 7.9 Hz) together (1H, NH), 7.51–6.86 (13H, m, Ar-H), 5.04 (s) and 5.02 (s) together (2H, CH$_2$OAr), 4.78 (2H, m, CHαthiopro+NCH$_A$H$_B$S), 4.47 (1H, m, CHαtyr), 4.46 (m) and 4.26 (m) together (1H, NCH$_A$H$_B$S), 3.62 (3H, s, CO$_2$Me), 3.52–2.68 (4H, m, CHCH$_2$S+CHCH$_2$Ar) and 2.02 (3H, s, COMe). m/z (ESI, 15V) 576 (M$^+$+1).

The following ester was prepared in a similar manner:
N-Phenylacetyl-D-thioproline-(O-benzyl)-L-tyrosine methyl ester δH (CDCl$_3$/CD$_3$OD 2:1) 7.18–6.61 (14H, m, Ar-H), 4.78 (2H, s, CH$_2$OPh), 4.72 (2H, m, CHα-thiopro+NCH$_A$H$_B$S), 3.45 (3H, s, CO$_2$Me) and 3.20–2.67 (4H, m, CHC$_2$AR+CHCH$_2$S). m/z (ESI, 15V) 519 (M$^+$+1).

EXAMPLE 46
N-(4'-Acetamidophenylacetyl)-D-thioproline-(O-benzyl)-L-tyrosine

A solution of the compound of Example 46 (275 mg, 0.48 mmol) in MeOH (2 ml), dioxan (2 ml), DMF (2 ml) and water (3 ml) was treated with LiOH (24 mg, 0.57 mmol) and stirred at room temperatue for 3 h, acidified with glacial acetic acid and concentrated in vacuo. The residue was triturated with water and the off-white solid isolated by filtration and dried in vacuo to give the title compound (150 mg, 56%). δH (DMSO-d$^6$) (2 rotameric species observed) 9.89 (1H, s, NHCOMe), 8.32 (br s) and 7.98 (br s), together (1H, NH), 7.52–6.82 (13H, Ar-H), 5.02 (s) and 4.97 (s) together (2H, CH$_2$OPh), 4.82 (2H, m, CHαthiopro+CHαtyr), 4.49–4.23 (2H, m, NCH$_2$S) and 3.56–2.70 (6H, m, CHCH$_2$Ar, COCH$_2$Ar, CHCH$_2$S). m/z (ESI, 60V) 562 (M$^+$+1).

The following compounds of Examples 47–61 were prepared in a similar manner to the compound of Example 46. Each starting ester was prepared according to the method of compound of Example 46.

EXAMPLE 47
N-Benzoyl-D-thioproline-(O-benzyl)-L-tyrosine

δH (CD$_3$OD) 8.12 (1H, brs, NH), 7.54–7.26 (10H, m, Ar-H), 7.11 (2H, ABd, J 8.5 Hz, CHCH$_2$Ar-H), 6.86 (2H, ABd, J 8.5 Hz, CHCH$_2$Ar-H), 5.01 (1H, m, CHαthiopro), 4.99 (2H, s, OCH$_2$Ph), 4.72–4.47 (3H, m, CHαtyr+NCH$_2$ S) and 3.22–2.79 (4H, m, CHCH$_2$S+CHCH$_2$Ar). m/z (ESI, 15V) 491 (M$^+$+1).

EXAMPLE 48
N-(2-Chloro-4-nitrobenzoyl)-D-thioproline-(O-benzyl)-L-tyrosine

δH (CD$_3$OD) (2 rotameric species observed) 8.36 (d, J 2.1 Hz) and 8.32 (d, J 2.1 Hz) together (1H, NO$_2$-Ar-H), 8.28 (d, J 2.1 Hz) and 8.25 (d, J 2.1 Hz) together (1G, NO$_2$-Ar-H), 7.65 (0.5H, d, J 8.4 Hz, NO$_2$-Ar-H), 7.42–7.23 (5.5H, m, PhCH$_2$O+NO$_2$Ar-H), 7.15 (d, J 8.7 Hz), and 7.05 (d, J 8.7 Hz) together (2H, ar-H), 6.88 (2H, m, Ar-H), 5.04 and 5.01 together (2H, s, CH$_2$OPh), 5.03 (1H, m, CHαthiopro), 4.71–4.29 (3H, m, CHαtyr+NCH$_2$S) and 3.37–2.68 (4H, m, CHCH$_2$S+CHCH$_2$Ar). m/z (ESI, 15V), 570 (M$^+$+1).

EXAMPLE 49
N-(Phenylaminocarbonyl)-D-thioproline-(O-benzyl)-L-tyrosine

δH (DMSO-$^6$d) 8.63 (1H, s, NHPh), 8.07 (1H, d, J 8.2 Hz, NH), 7.53–7.22 (9H, m, Ar-H), 7.11 (2H, ABd, J 8.4 Hz,

Ar-H), 6.97 (1H, m, Ar-H), 6.80 (2H, ABd, J 8.4 Hz, Ar-H), 4.97 (2H, CH$_2$OPh), 4.96 (1H, m, CHαThiopro), 4.80 (1H, d, J 8.8 Hz, NCH$_A$H$_B$S), 4.43 (1H, d, J 8.8 Hz, NCH$_A$H$_B$S), 4.42 (1H, m, CHα-tyr) and 3.05–2.83 (4H, m, CHCH$_2$Ar+CHCH$_2$S). m/z (ESI, 60V) 506 (M$^+$+1).

EXAMPLE 50

N-(tert-Butoxycarbonyl)-D-thioproline-(O-benzyl)-L-tyrosine

δH (DMSO-$^6$d) 8.22 (1H, br s, NH), 7.46–7.29 (5H, m, Ph), 7.11 (2H, ABd, J 8.4 Hz, Ar-H), 6.89 (2H, ABd, J 8.4 Hz, Ar-H), 5.05 (2H, s, CH$_2$OPh), 4.57 (1H, d, J 9.0 Hz, NCH$_A$H$_B$S), 4.49 (2H, m, CHαthiopro+CHαtyr), 4.22 (1H, d, J 9.0 Hz, NCH$_A$H$_B$S), 3.18–2.53 (4H, m, CHCH$_2$Ar+CHCH$_2$S) and 1.33 (9H, s, tBu). m/z (ESI, 15V) 487 (M$^+$+1).

EXAMPLE 51

N-Phenylacetyl-D-thioproline-(O-benzyl)-L-tyrosine

δH (DMSO-d$^6$) 2 rotameric species observed. 6.66–6.05 (14H, m, Ar-H), 4.23 (s) and 4.19 (s) together (2H, CH$_2$OPh), 4.03 (1H, m, CHαthiopro), 3.98–3.65 (3H, m, CHαtyr-NCH$_2$S), 2.72–2.01 (6H, m, COCH$_2$Ph, CHCH$_2$Ar, CHCH$_2$S). m/z (ESI, 15V) 505 (M$^+$+1).

EXAMPLE 52

N-Methylsulphonyl-D-thioproline-(O-benzyl)-L-tyrosine

δH (DMSO-d$^6$) 8.09 (1H, d, J 8.2 Hz, NH), 7.46–7.31 (5H, m, Ar-H), 7.12 (2H, ABd, J 8.5 Hz, Ar-H), 6.88 (2H, ABd, J 8.5 Hz, Ar-H), 5.05 (2H, s, CH$_2$OPh), 4.73 (1H, d, J 10.2 Hz, NCH$_A$H$_B$S), 4.72 (1H, m, CHαthiopro), 4.40 (1H, m, CHα-tyr), 4.29 (1H, d, J 10.2 Hz), 32.25 (1H, dd, J 11.4, 7.6 Hz, CHCH$_A$H$_B$S), 3.03 (3H, S, SO$_2$Me) and 3.02–2.86 (3H, m, CHCH$_A$H$_B$S, CHCH$_2$Ar). m/z (ESI, 15V), 465 (M$^+$+1).

EXAMPLE 53

N-Dimethylacetyl-D-thioproline-(O-2,6-dichlorobenzyl)-L-tyrosine

Found C, 54.25;H, 4.93; N, 5.22. C$_{24}$H$_{26}$Cl$_2$N$_2$O$_5$S. 0.3H$_2$O requires C, 54.24;H, 5.06; N, 5.27. m/z (ESI, 60V) 525, 527 (M$^+$+1).

EXAMPLE 54

N-(4-tert.Butoxycarbonylamino)butyryl-D-thioproline-(O-2,6-dichlorobenzyl)-L-tyrosine δH (DMSO-d$^6$) 8.39 (br s,) and 8.12 (br s) together (1H, NHBOC), 7.57–6.93 (7H, m, Ar-H), 6.80 (1B, br s, NH), 5.18 (2H, s, CH$_2$OPh), 4.83–4.20 (4H, m, CHαthiopro+CHαtyr+NCH$_2$S), 3.20–2.71 (6H, m, CHCH$_2$Ar+CHCH$_2$S+CH$_2$CO), 2.34 (2H, m, CH$_2$N, 1.61 (2H, m, CHCH$_2$N) and 1.36 (9H, s, tBu). m/z (ESI, 60V) 662 (M$^+$+23).

EXAMPLE 55

N-(4-Amino)butyryl-D-thioproline-(O-2,6-dichlorobenzyl)-L-tyrosine hydrochloride δH (DMSO-d$^6$) 7.96 *1H, br s, NH), 7.51–7.38 (3H, m, Cl$_2$-Ar-H), 7.18 (2H, ABd, J 8.7 Hz, ArH), 6.95 (2H, ABd, J 8.7 Hz, Ar-H), 5.25 (2H, s, CH$_2$OPh), 4.90 (1H, dd, J 7.4, 4.1 Hz, CHαthiopro), 4.54 (1H, d, J 9.2 Hz, NCH$_A$H$_B$S), 4.50 (1H, ddd, J 13.7, 8.4, 5.4 Hz, CH tyr), 4.41 (1H, d, J 9.2 Hz, NCH$_A$H$_B$S), 3.29–2.87 (6H, m, CHCH$_2$Ar+CHC$_2$S+CH$_2$CO), 2.49 (2H, M, CH$_2$NH$_2$) AND 1.88 (2H, M, CH$_2$CH$_2$N). M/Z (ESI, 60V) 540, 542 (M$^+$+1).

EXAMPLE 56

N-(3-tert.Butoxycarbonylamino)propionyl-D-thioproline-(O-2,6-dichlorobenzyl)-L-tyrosine δH (DMSO-d$^6$) 8.35 (br s) and 8.08 (br s) together (1H, NH), 7.56–7.43 (3H, m, Cl-$_2$ Ar-H), 7.15 (2H, br d, Ar-H), 6.96 (2H, ABd, J 6.4 Hz, Ar-H), 6.61 (br s) and 6.49 (br s) together (1H, NHCOO+ Bu), 5.19 (2H, s, CH$_2$OPh), 4.74 (2H, m, CHα-thiopro+NCH$_A$H$_B$S), 4.49–4.28 (2H, m, CHα-tyr+NCH$_A$H$_B$S), 3.32–2.71 (8H, n, CHCH$_2$Ar+CHCH$_2$S+COCH$_2$+CH$_2$NH) and 1.36 (9H, s, +tBu). m/z (ESI, 30V) 648, 650 (M$^+$+Na).

EXAMPLE 57

N-(3-Amino)propionyl-D-thioproline-(O-2,6-dichlorobenzyl)-L-tyrosine hydrochloride δH (DMSO-d$^6$) 8.02 (1H, br s, NH), 7.51–7.39 (3H, m, Cl$_2$-r-H), 7.18 (2H, ABd, Ar-H), 6.96 (2H, ABd, Ar-H), 5.25 (2H, s, CH$_2$OPh), 4.91 (1H, dd, 7.3, 3.9 Hz, CHα-thiopro), 4.77 (1H, d, J 9.1 Hz, NCH$_A$H$_B$S), 4.52 (1H, m, CHα-tyr), 4.32 (1H, d, J 9.1 Hz, NCH$_A$H$_B$S), 3.30–2.52 (8H, m, CHCH$_2$Ar+CHCH$_2$S+CH$_2$CO+CH$_2$NH$_2$). m/z (ESI, 60V) 526, 528 (M$^+$+1).

EXAMPLE 58

N-(3-Carboxy)propionyl-D-thioproline-(O-2,6-dichlorobenzyl)-L-tyrosine methyl ester δH (DMSO-d$^6$,) 7.88 (1H, br s, NH), 7.51–7.38 (3H, m, Cl$_2$-Ar-H), 7.14 (2H, ABd, J 8.7 Hz, Ar-H), 6.97 (2H, ABd, J 8.7 Hz, Ar-H), 5.26 (2H, s, CH$_2$OPh), 4.88 (1H, dd, J 7.3, 3.8 Hz, CHα-thiopro), 4.80 (1H, d, J 9.1 Hz, NCH$_A$H$_B$S), 4.56 (1H, ddd, J 14.0, 8.4, 5.7 Hz, CHα-tyr), 4.40 (1H, d, J 9.1 Hz, NCH$_A$H$_B$S), 3.65 (3H, s, CO$_2$Me), 3.27–2.91 (4H, m, CHCH$_2$Ar+CHCH$_2$S) and 2.55 (4H, m, CH$_2$CH$_2$CO$_2$H). m/z (ESI, 60V) 569, 571 (M$^+$+1).

EXAMPLE 59

N-(3-Carboxy)propionyl-D-thioproline-(O-2,6-dichlorobenzyl)-L-tyrosine

δH (DMSO-d$^6$) 7.70 (1H, br s, NH), 7.52–7.39 (3H, m, Cl$_2$-Ar-H), 7.16 (2H, ABd, J 8.6 Hz, Ar-H), 6.96 (2H, ABd, J 8.6 Hz, Ar-H), 5.25 (2H, s, CH$_2$OPh), 4.88 (1H, dd, J 7.4, 3.8 Hz, CHαthiopro), 4.81 (1H, d, J 9.1 Hz, NCH$_{AB}$S), 4.49 (1H, m, CHαtyr), 4.39 (1H, d, J 9.1 Hz, NCH$_A$H$_B$S), 3.26–2.88 (4H, m, CHCH$_2$Ar+CHCH$_2$S), 2.57 (4H, m, CH$_2$CH$_2$CO$_2$H). m/z (ESI, 60V) 555, 557(M$^+$+1).

EXAMPLE 60

N-(2-Methylpropyl)oxycarbonyl-D-thioproline-(O-benzyl)-L-tyrosine

δH (DMSO-d$^6$, 390K) 7.64 (1H, br d, NH), 7.37 (5H, m, Ph-H), 7.11 2H, ABd, J 8.7 Hz, Ar-H), 6.90 (2H, ABd, J 8.7 Hz, Ar-H), 5.07 (2H, s, CH$_2$OPh), 4.69 (1H, m, CHα-thiopro), 4.69 (1H, d, J 9.0 Hz, NCH$_A$H$_B$S), 4.46 (1H, m, CHαtyr), 4.32 (1H, d, J 9.0 Hz, NCH$_A$H$_B$S), 3.82 (2H, d, J 6.4 Hz, OCH$_2$CH), 3.23 (1H, dd, J 11.5, 7.4 Hz, CHCH$_A$H$_B$S), 3.05 (1H, dd, J 11.0, 5.4 Hz, CHCH$_A$H$_B$Ar), 2.89 (2H, m, CHCH$_A$H$_B$S+CHCH$_A$H$_B$Ar), 21,87 (1H, m, CHMe$_2$), 0.90 (3H, s, Me) and 0.88 (3H, s, Me). m/z (ESI, 60V), 487 (M$^+$+1).

EXAMPLE 61

N-(3,4,5-Trimethoxyphenyl)acetyl-D-thioproline-(O-benzyl)-L-tyrosine

δH (DMSO-d$^6$, 390K) 7.74 (1H, br s, NH), 7.42–7.29 (5H, m, Ar-H), 7.12 (2H, ABd, J 8.6 Hz, ArH), 6.90 (2H, ABd, J 8.6 Hz, Ar-H), 6.54 (2H, s, MeO$_3$-Ar-H), 5.06 (2H, s, CH$_2$OPh), 4.89 (1H, m, CHα-thiopro), 4.83 (1H, d, J 9.2 Hz, NCH$_A$H$_B$S), 4.49 (1H, m, CHαtyr), 4.38 (1H, d, J 9.2

Hz, NCH$_A$H$_B$S), 3.72 (6H, s, OMe), 3.70 (3H, s, OMe), 3.65–3.53 (2H, m, CH$_2$CO), 3.25–2.86 (4H, m, CHCH$_2$S+ CHCH$_2$Ar. m/z (ESI, 60V), 612 (M$^+$+1).

The following assays can be used to demonstrate the potency and selectivity of the compounds according to the invention. In each of these assays an IC$_{50}$ value was determined for each test compound and represents the concentration of compound necessary to achieve 50% inhibition of cell adhesion where 100%=adhesion assessed in the absence of the test compound and 0%=absorbance in wells that did not receive cells.

$\alpha_4\beta_1$ Integrin-dependent Jurkat cell adhesion to VCAM-Ig 96 well NUNC plates were coated with F(ab)$_2$ fragment goat anti-human IgG Fcγ-specific antibody [Jackson Immuno Research 109-006-098: 100 μl at 2 μg/ml in 0.1M NaHCO$_3$, pH 8.4], overnight at 4°. The plates were washed (3×) in phosphate-buffered saline (PBS) and then blocked for 1 h in PBS/1% BSA at room temperature on a rocking platform. After washing (3× in PBS) 9 ng/ml of purified 2 d VCAM-Ig diluted in PBS/1% BSA was added and the plates left for 60 minutes at room temperature on a rocking platform. The plates were washed (3× in PBS) and the assay then performed at 370 for 30 min in a total volume of 200 μl containing 2.5×10$^5$ Jurkat cells in the presence or absence of titrated test compounds.

Each plate was washed (2×) with medium and the adherent cells were fixed with 100μl methanol for 10 minutes followed by another wash. 100 μl 0.25% Rose Bengal (Sigma R4507) in PBS was added for 5 minutes at room temperature and the plates washed (3×) in PBS. 100μl 50% (v/v) ethanol in PBS was added and the plates left for 60 min after which the absorbance (570 nm) was measured.

$\alpha_4\beta_7$ Integrin-dependent JY cell adhesion to MAdCAM-Ig

This assay was performed in the same manner as the $\alpha_4\beta_1$ assay except that MAdCAM-Ig (150 ng/ml) was used in place of 2 d VCAM-Ig and a sub-line of the β-lympho blastoid cell-line JY was used in place of Jurkat cells. The IC$_{50}$ value for each test compound was determined as described in the $\alpha_4\beta_1$ integrin assay.

$\alpha_5\beta_1$ Integrin-dependent K562 cell adhesion to fibronectin 96 well tissue culture plates were coated with human plasma fibronectin (Sigma F0895) at 5 μg/ml in phosphate-buffered saline (PBS) for 2 hr at 37° C. The plates were washed (3× in PBS) and then blocked for 1 h in 100 μl PBS/1% BSA at room temperature on a rocking platform. The blocked plates were washed (3× in PBS) and the assay then performed at 37° C. in a total volume of 200 μl containing 2.5×10$^5$ K562 cells, phorbol-12-myristate-13-acetate at 10 ng/ml, and in the presence or absence of titrated test compounds. Incubation time was 30 minutes. Each plate was fixed and stained as described in the $\alpha_4\beta_1$ assay above.

$\alpha_m\beta_2$-dependent human polymorphonuclear neutrophils adhesion to plastic 96 well tissue culture plates were coated with RPMI 1640/10% FCS for 2 h at 37° C. 2×10$^5$ freshly isolated human venous polymorphonuclear neutrophils (PMN) were added to the wells in a total volume of 200 μl in the presence of 10 ng/ml phorbol-12-myristate-13-acetate, and in the presence or absence of test compounds, and incubated for 20 min at 37° C. followed by 30 min at room temperature. The plates were washed in medium and 100 μl 0.1% (w/v) HMB (hexadecyl trimethyl ammonium bromide, Sigma H5882) in 0.05M potassium phosphate buffer, pH 6.0 added to each well. The plates were then left on a rocker at room temperature for 60 min. Endogenous peroxidase activity was then assessed using tetramethyl benzidine (TMB) as follows: PMN lysate samples mixed with 0.22% H$_2$O$_2$ (Sigma) and 50 μg/ml TMB (Boehringer Mannheim) in 0.1M sodium acetate/citrate buffer, pH 6.0 and absorbance measured at 630 nm.

αIIb/β$_1$ -dependent human platelet aggregation

Human platelet aggregation was assessed using impedance aggregation on the Chronolog Whole Blood Lumiaggregometer. Human platelet-rich plasma (PRP) was obtained by spinning fresh human venous blood anticoagulated with 0.38% (v/v) tri-sodium citrate at 220× g for 10 min and diluted to a cell density of 6×10$^8$/ml in autologous plasma. Cuvettes contained equal volumes of PRP and filtered Tyrode's buffer (g/liter: NaCl 8.0; MgCl$_2$.H$_2$O 0.427; CaCl$_2$ 0.2; KCl 0.2; D-glucose 1.0; NaHCO$_3$ 1.0; NaHPO$_4$.2H$_2$O 0.065). Aggregation was monitored following addition of 2.5 μM ADP (Sigma) in the presence or absence of inhibitors.

In the above assays the compounds of the invention generally have IC$_{50}$ values in the $\alpha_4\beta_1$ and $\alpha_4\beta_7$ assays of 1 μM and below. The compounds of the Examples typically had IC$_{50}$ values of 500 nM and below in these assays. In the other assays featuring α integrins of other subgroups the same compounds had IC$_{50}$ values of 50 μM and above thus demonstrating the potency and selectivity of their action against the binding of the $\alpha_4$ integrins to their ligands.

What is claimed is:

1. A compound of formula (1):

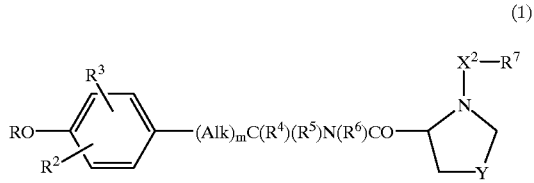

(1)

wherein:

R is (1) a group $R^1X^1$— where $R^1$ is an optionally substituted alkyl or aromatic group, and $X^1$ is a covalent bond or a —$(CH_2)_n$— (where n is an integer 1 or 2), —C(O)—, —$CH_2$C(O)—, —NHC(O)—, —$CH_2$NHC(O)—, or —$SO_2$— group, or (2) a group $(Hal^1)_3CSO_2$—, where $Hal^1$ is a fluorine or chlorine atom;

$R^2$ and $R^3$, which may be the same or different, is each a hydrogen or halogen atom or an alkyl, alkoxy, hydroxyl or nitro group;

Alk is an alkylene chain;

m is zero or an integer 1;

$R^4$ is a hydrogen atom or a methyl group;

$R^5$ is a group —$(CH_2)_pCO_2R^8$ where p is zero or an integer 1 and $R^8$ is a hydrogen atom or an alkyl group;

$R^6$ is a hydrogen atom or an alkyl group;

Y is a sulfur atom or a —$S(O)_q$ group where q is an integer 1 or 2;

$X^2$ is a —C(O)—, —C(O)O—, —C(O)NH— or —$SO_2$— group;

$R^7$ is an optionally substituted alkyl group or an aryl or aralkyl group;

or a salt, solvate or hydrate thereof.

2. A compound according to claim 1 wherein $R^5$ is a —$CH_2CO_2H$ or —$CO_2H$ group.

3. A compound according to claim 2 wherein $R^5$ is a —$CO_2H$ group.

4. A compound according to claim 1 wherein Y is a sulphur atom.

5. A compound according to claim 1 wherein $R^4$ and $R^6$ is each a hydrogen atom.

6. A compound according to claim 1 wherein Alk is a —$CH_2$— chain and m is the integer 1.

7. A compound according to claim 1 wherein R is a $R^1X^1$ group.

8. A compound according to claim 7 wherein $X^1$ is a —$CH_2$— or —C(O)— group.

9. A compound according to claim 7 wherein $R^1$ is an optionally substituted phenyl group.

10. A compound according to claim 1 wherein $X^2$ is a —C(O)— group.

11. A compound according to claim 1 wherein $R^7$ is an optionally substituted $C_{1-3}$alkyl or benzyl group.

12. A compound according to claim 11 wherein $R^7$ is a methyl group.

13. A compound which is selected from the group consisting of:

N-Acetyl-D-thioproline-(O-2,6-dichlorobenzyl)-L-tyrosine;

N-Acetyl-D-thioproline-(O-2,4,6-trichlorobenzyl)-L-tyrosine;

N-Acetyl-D-thioproline-(O-2,6-difluorobenzyl)-L-tyrosine;

N-Acetyl-D-thioproline-(O-2,6-dichlorobenzyl)-3-nitro-L-tyrosine;

N-(3-Carboxy)propionyl-D-thioproline-(O-2,6-dichlorobenzyl)-L-tyrosine; and

N-Acetyl-D-thioproline-(O-2,4,6-trichlorobenzoyl)-L-tyrosine;

or a salt, solvate or hydrate thereof.

14. A pharmaceutical composition comprising a compound according to claim 1 together with one or more pharmaceutically acceptable carriers, excipients or diluents.

15. A method for the prophylaxis or treatment of a disease or disorder in a mammal in which the extravasation of leukocytes plays a role, comprising administering to a mammal suffering from such a disease or disorder a therapeutically effective amount of a compound according to claim 1.

16. A method according to claim 15 wherein said disease or disorder is selected from the group consisting of inflammatory arthritis, multiple sclerosis, allograft rejection, diabetes, inflammatory dermatoses, asthma and inflammatory bowel disease.

17. A method for modulating levels of early haematopoichic cells circulating in the bloodstream of a mammal, comprising administering to the mammal an effective amount of a compound according to claim 1.

18. A method according to claim 17 wherein the haematopoichic cells comprise stem cells.

19. A method for inhibiting, in a mammal, the binding of $\alpha 4$ integrins to the ligands thereof, comprising administering to the mammal an effective amount of a compound according to claim 1.

20. A method according to claim 19 wherein the $\alpha 4$ integrins are selected from the group consisting of $\alpha 4\beta 1$ and $\alpha 4\beta 7$ integrins.

* * * * *